United States Patent
Onimura

(10) Patent No.: US 8,094,319 B2
(45) Date of Patent: Jan. 10, 2012

(54) IMAGE DIAGNOSTIC APPARATUS AND METHOD

(75) Inventor: Yuuji Onimura, Hadano (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 656 days.

(21) Appl. No.: 12/207,976

(22) Filed: Sep. 10, 2008

(65) Prior Publication Data

US 2009/0073455 A1    Mar. 19, 2009

Related U.S. Application Data

(60) Provisional application No. 60/976,045, filed on Sep. 28, 2007.

(30) Foreign Application Priority Data

Sep. 10, 2007 (JP) ................................. 2007-234681

(51) Int. Cl.
*G01B 9/02* (2006.01)
(52) U.S. Cl. ...................................................... 356/479
(58) Field of Classification Search .................. 356/479, 356/497
See application file for complete search history.

(56) References Cited

U.S. PATENT DOCUMENTS

| | | | | |
|---|---|---|---|---|
| 5,029,016 A * | 7/1991 | Hiyama et al. | ................. | 358/403 |
| 5,124,789 A * | 6/1992 | Hiyama et al. | ................. | 348/74 |
| 6,621,574 B1 * | 9/2003 | Forney et al. | ................. | 356/301 |
| 7,075,658 B2 * | 7/2006 | Izatt et al. | ................. | 356/479 |
| 7,158,234 B2 * | 1/2007 | Uchiyama et al. | ................. | 356/479 |
| 7,365,859 B2 * | 4/2008 | Yun et al. | ................. | 356/497 |
| 7,548,320 B2 * | 6/2009 | Chan et al. | ................. | 356/497 |
| 7,852,484 B2 * | 12/2010 | Teramura | ................. | 356/479 |
| 2004/0181148 A1 * | 9/2004 | Uchiyama et al. | ................. | 600/425 |
| 2005/0036150 A1 * | 2/2005 | Izatt et al. | ................. | 356/479 |
| 2005/0206906 A1 * | 9/2005 | Chan et al. | ................. | 356/497 |
| 2006/0055939 A1 * | 3/2006 | Akiba et al. | ................. | 356/497 |
| 2006/0079762 A1 * | 4/2006 | Norris et al. | ................. | 600/427 |
| 2007/0081166 A1 * | 4/2007 | Brown et al. | ................. | 356/479 |
| 2007/0187632 A1 * | 8/2007 | Igarashi | ................. | 250/559.36 |
| 2007/0232902 A1 * | 10/2007 | Teramura | ................. | 600/425 |
| 2009/0073455 A1 * | 3/2009 | Onimura | ................. | 356/479 |
| 2009/0143686 A1 * | 6/2009 | Onimura et al. | ................. | 600/477 |
| 2009/0247878 A1 * | 10/2009 | Tanioka et al. | ................. | 600/462 |
| 2010/0130872 A1 * | 5/2010 | Irisawa | ................. | 600/478 |
| 2010/0210937 A1 * | 8/2010 | Tearney et al. | ................. | 600/424 |

FOREIGN PATENT DOCUMENTS

JP   2006-015134 A   1/2006

* cited by examiner

*Primary Examiner* — Gregory J Toatley
*Assistant Examiner* — Scott Richey
(74) *Attorney, Agent, or Firm* — Buchanan Ingersoll & Rooney P.C.

(57) ABSTRACT

An image diagnostic apparatus includes a probe capable of light transmission and reception, wherein a reflection light is obtained from the probe by scanning the probe rotatingly, and a tomographic image is formed and outputted based on the obtained reflection light. A light-shield is provided to shield the light transmitted to the probe, a connection detector detects whether or not the probe is connected, and a controller controls the light-shield based on a detected result by the connection detector.

18 Claims, 26 Drawing Sheets

IMAGE DIAGNOSTIC APPARATUS AND METHOD

This application is based on and claims priority under 35 U.S.C. §119(e) with respect to U.S. Provisional Application No. 60/976,045 filed on Sep. 28, 2007, the entire content of which is incorporated herein by reference. This application is also based on and claims priority under 35 U.S.C. §119(a) with respect to Japanese Patent Application 2007-234681 filed Sep. 10, 2007, the entire content of which is hereby incorporated by reference.

TECHNOLOGICAL FIELD

The present invention generally relates to an image diagnostic apparatus and a method.

BACKGROUND DISCUSSION

In the past, an optical coherent tomography diagnosis apparatus (OCT: Optical Coherent Tomography) has been used as an image diagnostic apparatus for arteriosclerosis diagnosis to diagnose before surgery under an endovascular treatment by a high performance catheter such as a balloon catheter, a stent and the like or for confirming the results of such treatment.

An optical coherent tomography diagnosis apparatus is an apparatus in which, in a state in which a catheter with a built-in optical lens and an optical fiber mounted with an optical mirror at the distal tip thereof is inserted into a blood vessel, measuring light is light-emitted in the blood vessel while rotating the optical mirror, and radial scanning is carried out by receiving reflected light from biological tissue. A tomographic image of the blood vessel is created based on the coherent light by making interference between the obtained reflection light and reference light divided from the measuring light beforehand.

Further, an optical coherent tomography diagnosis apparatus has recently been diagnosed which utilizes wavelength-sweeping for an improvement type of optical coherent tomography diagnosis apparatus.

The basic structure of the wavelength-sweeping optical coherent tomography diagnosis apparatus is similar to that of the optical coherent tomography diagnosis apparatus (OCT), but one aspect involves the use of a light source having a longer wavelength than that of the optical coherent tomography diagnosis apparatus and also lights having different wavelengths are light-emitted continuously. The mechanism for varying the light path length of the reference light is made unnecessary by obtaining reflection light intensity at each point in the depth direction of the biological tissue by using frequency analysis of the coherent light.

Any of the optical coherent tomography diagnosis apparatus mentioned above has a characteristic that the stronger the intensity of the emitted measuring light, the more clear the extracted tomographic image becomes. It is thus desirable, on the occasion of measurement, to use the apparatus by raising the intensity of the measuring light as much as possible in a range not injuring the biological tissue.

However, problems arise when the apparatus is used by raising the intensity of the measuring light. Generally, the light source of the optical coherent tomography diagnosis apparatus requires a certain amount of time for the start-up. Therefore, upon diagnosis a catheter is inserted into a blood vessel usually in a state in which the light source is activated beforehand. In other words, when inserting the catheter into the blood vessel, it is in a state in which the measuring light is already being emitted from the distal portion thereof and so it happens on the occasion of diagnosis that the measuring light is illuminated continuously at the periphery of the apparatus.

Here, the measuring light used in the optical coherent tomography diagnosis apparatus is generally a near-infrared ray and is invisible to human eyes, so if an individual (i.e., the eyes of an individual) is subjected to the illumination, it cannot be expected that the individual will react to avoid the illumination. For this reason, it is considered that some sort of influence (undesirable influence) will occur before and after the diagnosis, for example in a case in which the measuring light is illuminated by chance continuously on the eyes of persons in the surrounding area.

Also, with respect to a test subject, the measuring light will illuminate the same position of a biological tissue continuously during the diagnosis in a case in which the rotation of the optical mirror stops in a state in which the catheter is inserted into a blood vessel or the like.

In such a case, even if the intensity of the emitted measuring light is suppressed within a range not damaging to the biological tissue, some amount of influence is exerted on the biological tissue as a result of being illuminated continuously.

A proposal has been made, for example in a Patent Document 1 (Japanese unexamined Publication No. 2006-15134), in which a state of attachment and detachment for a probe is detected and in a case in which it is judged that the probe is not connected, the drive of the light source is stopped.

However, the light source of the optical coherent tomography diagnosis apparatus requires a long time period from a stop state to a state in which it becomes possible to supply a stable light. If the light source is activated after detecting the state of attachment and detachment for the probe, a lot of time may be required until it reaches a usable state.

SUMMARY

According to one aspect, an image diagnostic apparatus comprises a light source, a probe connected to the light source to transmit light from the light source and receive reflection light in a body cavity by rotatingly scanning the probe in the body cavity to permit formation of a tomographic image in the body cavity based on the reflection light, a first branch portion for branching the light transmitted to the probe, a sample light path branched on the sample side by the first branch portion, a reference light path branched on the reference side by the first branch portion, and a light transmission permitting and preventing device positioned along the sample light path. In addition, a control unit is connected to the light transmission permitting and preventing device for controlling the light transmission permitting and preventing device to either permit the light at the incident port of the light transmission permitting and preventing device to exit out of the emission port or to prevent light at the incident port from exiting out of the emission port. The light transmission permitting and preventing device comprises one of i) a shutter unit in which a movable shutter is positioned in a housing and is controlled by the control unit to move between one position permitting the light at the incident port to exit out of the emission port and another position preventing light at the incident port from exiting out of the emission port; ii) and a frequency shifter unit controlled by the control unit to shift a frequency of light at the input port to either permit or prevent the light at the inlet port to exit the frequency shifter at the emission port.

According to another aspect, an image diagnostic apparatus comprises a probe adapted to be connected to a light source to transmit light from the light source and receive reflection light in a body cavity by rotatingly scanning the probe in the body cavity to permit formation of a tomographic image in the body cavity based on the reflection light, a light-shield positioned upstream of the probe with respect to a direction of light transmission to selectively shield the probe from the light from the light source, a connection detector for detecting whether or not the probe is connected, and a controller connected to the light shield to control the light-shield based on a result detected by the connection detector to either shield the probe from the light from the light source or permit the light to transmit to the probe.

Also disclosed here is a method of operating an image diagnostic apparatus in which a probe positioned in a body cavity transmits light from a light source and receives reflection light in the body cavity by rotatingly scanning the probe in the body cavity to permit formation of a tomographic image in the body cavity based on the reflection light. The method comprises detecting whether the probe is connected to the light source, and using a result of the detection of whether the probe is connected to the light source to determine whether to permit the light to be transmitted to the probe or to prevent the light from being transmitted to the probe.

BRIEF DESCRIPTION OF THE DRAWING FIGURES

DETAILED DESCRIPTION

Set forth below, by way of example, is a description of various embodiments of an optical coherent tomography diagnosis apparatus, with reference to the accompanying drawings.

First Exemplified Embodiment

1. Measurement Principle of Optical Coherent Tomography Diagnosis Apparatus

First, a description is set forth of the measurement principle of an optical coherent tomography diagnosis apparatus. Generally, light is an electromagnetic wave and so it has a characteristic of exerting interference in case of being superimposed. Interference performance of easy-to-interfere or hard-to-interfere is also referred to as coherence and in a general optical coherent tomography diagnosis apparatus, coherent light having low coherence (low coherent light) is utilized.

Figure 1:
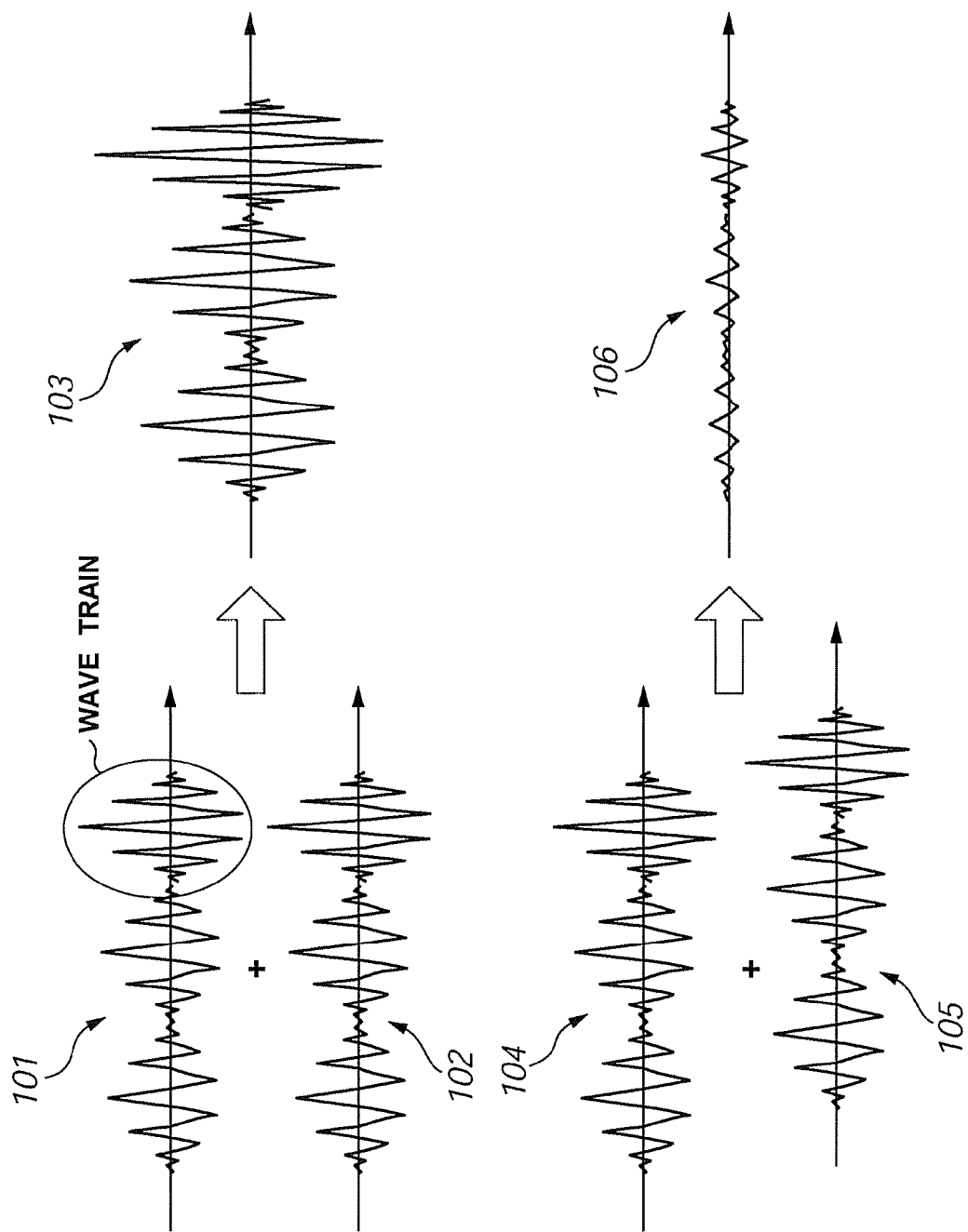
FIGS. 1A and 1B are diagrams explaining a measurement principle of an optical coherent tomography diagnosis apparatus.

The low coherent light becomes a random signal as shown by 101, 102 in FIG. 1A, where time is represented along the horizontal axis and the electric field is represented along the vertical axis. Respective peaks in the same drawing are referred to as a wave train and the respective wave trains possess mutually independent phases and amplitudes. For this reason, as shown in FIG. 1A, in a case in which the same wave trains overlap, constructive interference (between 101 and 102) occurs and the two waves are additive in effect (see 103). On the other hand, in a case in which there is a very little time delay (between 104 and 105 in FIG. 1B), cancellation of the two waves tends to occur and a constructive interference will not be observed (see 106 in FIG. 1B). Rather a sort of destructive interference occurs in which the two waves tend to counteract one another.

Figure 2:
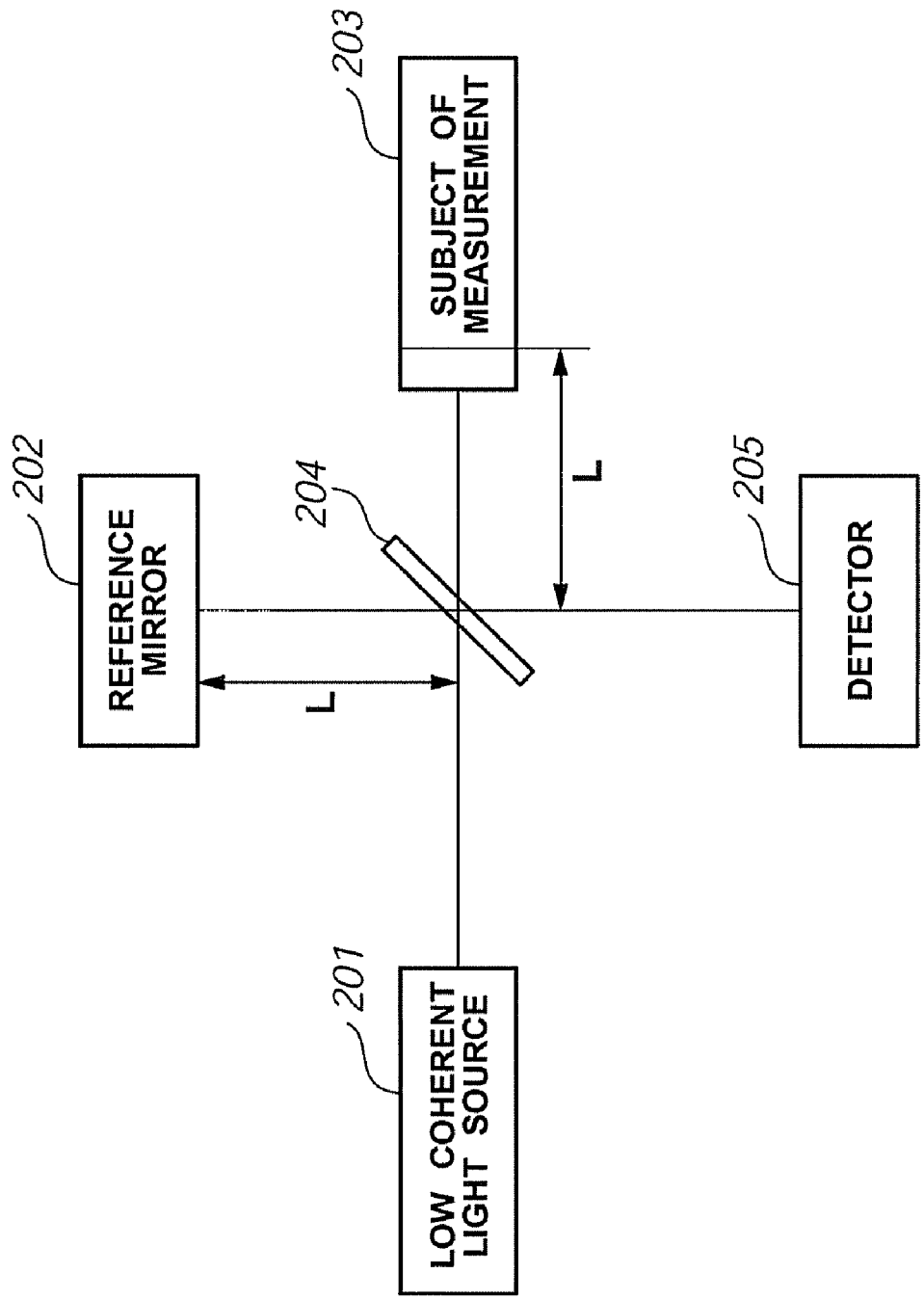
FIG. 2 is a schematic illustration of the basic principle of an optical coherent tomography diagnosis apparatus.

The optical coherent tomography diagnosis apparatus is an apparatus utilizing this characteristic, and FIG. 2 shows a basic principle of the apparatus. As shown in FIG. 2, light outputted from a low coherent light source 201 is split by a beam splitter 204 and the respective beams are directed to a reference mirror 202 and a subject of measurement 203. At that time, reflection (reflected) light returned from the subject of measurement side include reflection (reflected) light from various positions such as light reflected by a material body surface, light reflected by a shallow position inside the material body, light reflected by a deep portion inside the material body, etc.

However, the incident light is a low coherent light, so that when the distance from the beam splitter 204 to the reference mirror 202 is L and coherent length is ΔL, the reflected light whose interference can be observed becomes only a reflected light from a reflection surface which exists at a position whose distance from the beam splitter 204 is L+ΔL/2.

Consequently, if the distance from the beam splitter 204 to the reference mirror 202 is changed, it is possible for the detector 205 to selectively detect only the reflection light from the reflection surface inside the material body corresponding to the distance thereof. Then, it is possible, based on the intensity of the reflection light in response to each distance, to form a tomographic image by making structure information inside the material body visible.

2. Appearance Configuration of Optical Coherent Tomography Diagnosis Apparatus

Figure 3:
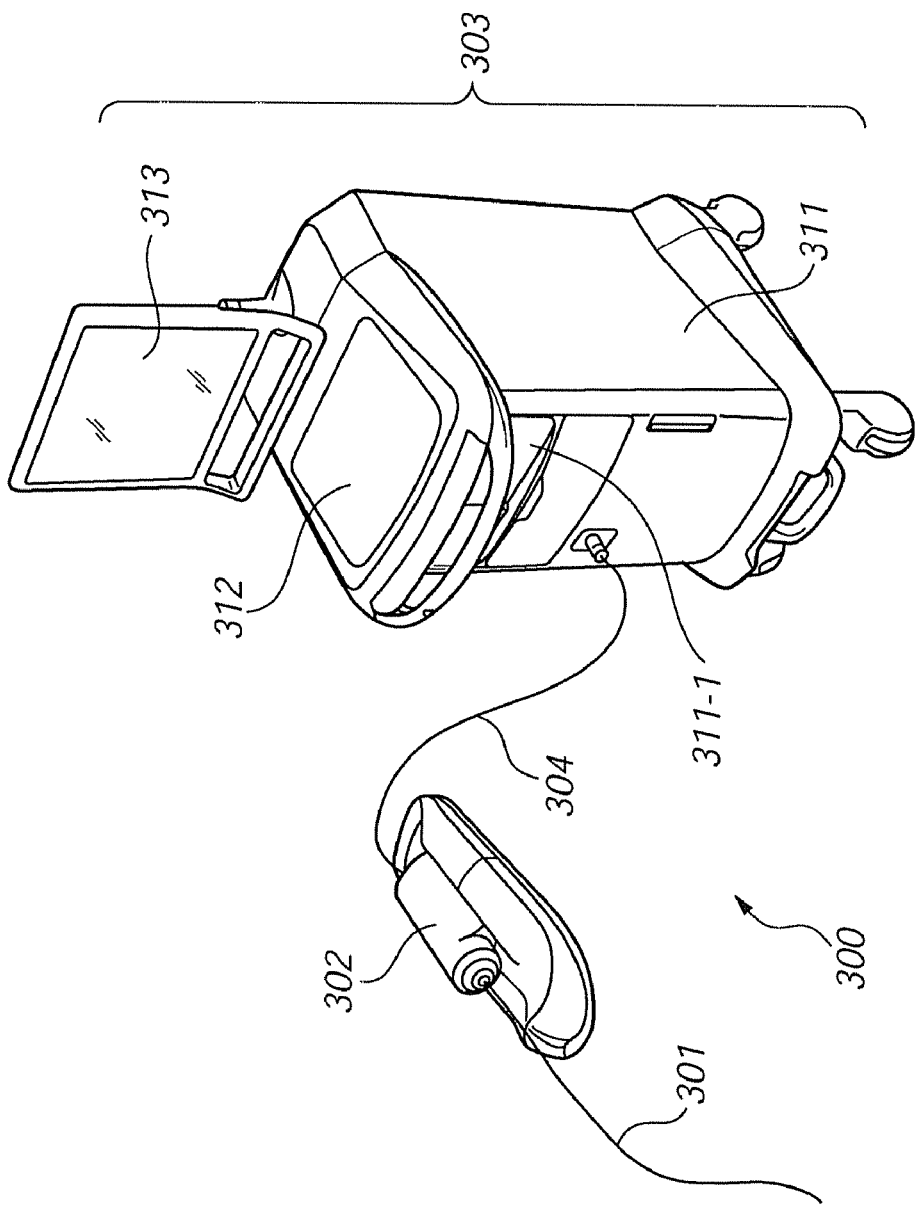
FIG. 3 is a general perspective view of an optical coherent tomography diagnosis apparatus.

FIG. 3 schematically illustrates the appearance of the optical coherent tomography diagnosis apparatus according to a first exemplified embodiment.

As shown in FIG. 3, the optical coherent tomography diagnosis apparatus 300 includes a catheter unit 301, a scanner/pullback unit 302 and an operation control unit 303. The scanner/pullback unit 302 and the operation control unit 303 are connected by a signal wire 304.

The catheter unit 301 is inserted into a blood vessel directly and measures a state inside the blood vessel by using an optical probe. The scanner/pullback unit 302 defines the radial operation of the optical probe in the catheter unit 301.

When executing an optical coherence tomography diagnosis in the blood vessel, the operation control unit 303 functions to permit input of various kinds of setting values and to process data obtained by the measurement and for displaying the data as a tomographic image.

The operation control unit 303 includes a main body control unit 311 which, for example, processes the data obtained by the measurement and outputs the processed result. The operation control unit 303 also includes a printer/DVD-recorder 311-1 which, for example, prints the processed result in the main body control unit 311, and stores it as data.

The operation control unit 303 further includes an operation panel 312 through which the user executes the input of various kinds of setting values, and an LCD monitor 313 which displays the process result in the main body control unit 311.

3. Features of Optical Coherent Tomography Diagnosis Apparatus

Figure 4:
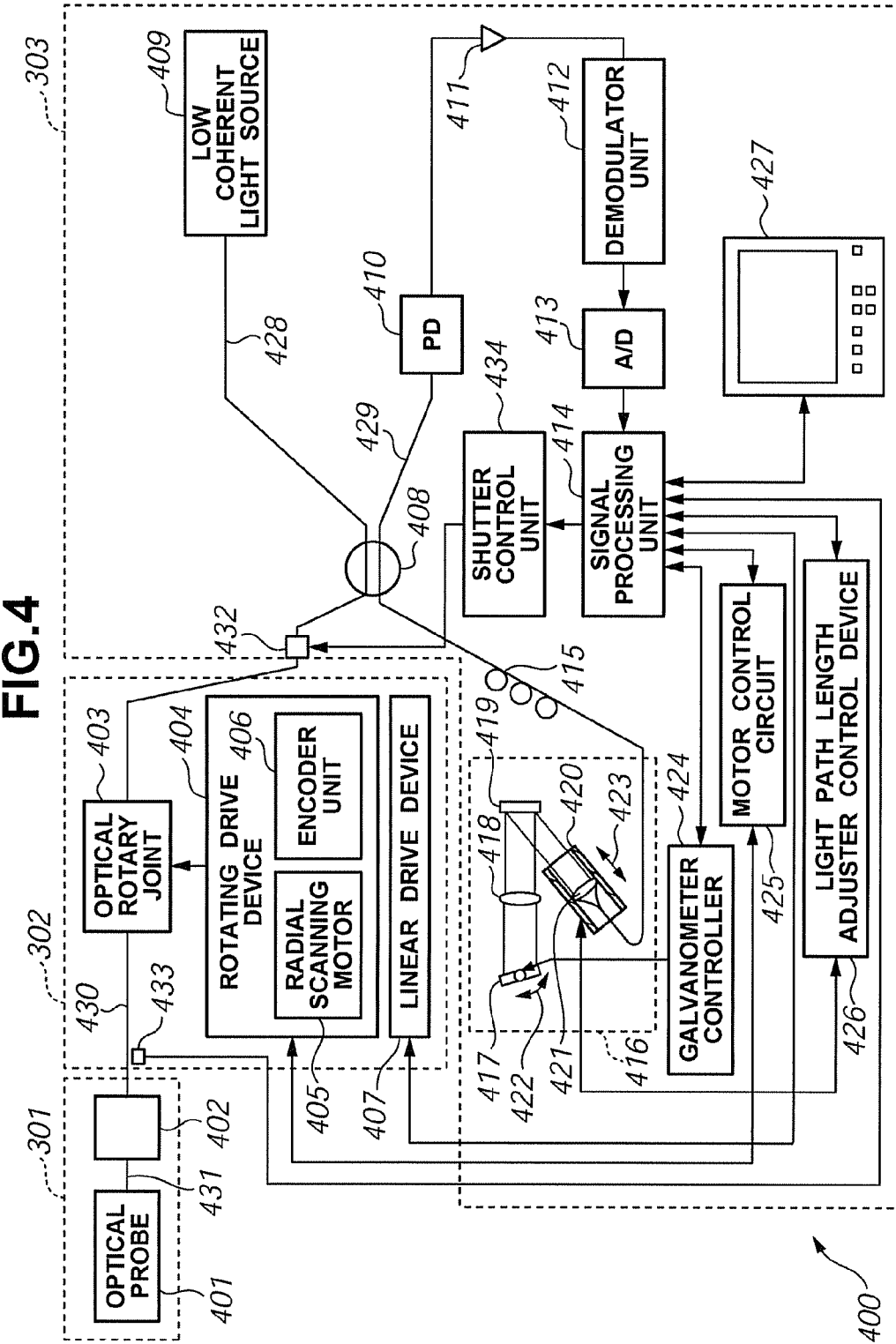
FIG. 4 is a schematic illustration of aspects of an optical coherent tomography diagnosis apparatus according to a first exemplified embodiment disclosed here.

FIG. 4 illustrates a functional constitution of the optical coherent tomography diagnosis apparatus 300 according to this first exemplified embodiment.

The apparatus 300 includes a low coherent light source 409 such as, for example, a super high luminosity light-emitting diode. The low coherent light source 409 outputs a low coherent light which shows coherence only in a short distance range such that the wavelength thereof is around 1310 nm and the coherent distance (coherent length) thereof is around a few μms to a few tens of μms.

For this reason, in a case in which this light is split into two paths and the two paths are thereafter mixed together again, and in a case in which the difference of the two light path lengths from the splitting point to the mixing point is within a short distance range such as around 17 μm, it is detected as a coherent light, and in a case in which the difference of the light path lengths is larger than that, the coherent light cannot be detected.

The light of the low coherent light source 409 enters one end of a first single-mode fiber 428 and is transmitted to the distal surface side of the fiber 428. The first single-mode fiber 428 is coupled optically with a second single-mode fiber 429 at an optical coupler unit 408. The optical coupler unit 408 refers to an optical component which can, for example, split one light signal into two or more outputs, and can combine two or more inputted light signals into one output. The light of the low coherent light source 409 is split into two paths by the optical coupler unit 408 and is transmitted thereby. The optical coupler 408 constitutes an example of a branch portion at which is branched the light transmitted from the source to the probe.

A shutter unit 432 is provided on the distal side of the optical coupler unit 408 of the first single-mode fiber 428. The shutter unit 432 controls the light emission from the operation control unit 303 to the scanner/pullback unit 302 side.

The inside of the scanner/pullback unit 302 is provided with an optical rotary joint 403 for attaining coupling between a non-rotating portion and a rotating portion, and for transmitting the light.

Further, the distal tip of a third single-mode fiber 430 in the optical rotary joint 403 is detachably connected to a connector portion 402 of the optical probe. Thus, the light is transmitted from the low coherent light source 409 to a fourth single-mode fiber 431 which is inserted into (positioned in) the optical probe 401 for effecting repeated light transmission and reception and which is rotatingly drivable. The light path between the optical coupler unit 408 and the optical probe constitutes a sample light path.

The attachment and detachment of the connector portion 402 of the optical probe is detected by a catheter connection detector unit 433 and the detected result is inputted to a signal processing unit 414. In the signal processing unit 414, an instruction for controlling the shutter unit 432 is outputted to the shutter control unit 434 based on the inputted detected result, and in the shutter control unit 434, the operation of the shutter unit 432 is controlled based on the instruction. In other words, the shutter unit 432 operates to shield the light transmitted from the operation control unit 303 with respect to the optical probe 401.

The light transmitted while the shutter unit 432 is opened is illuminated while being scanned radially from the distal side of the optical probe 401 to the biological tissue side in the body cavity. Then, a portion of the reflected lights diffused on the surface or in the inside of the biological tissue side is taken-in or received by the optical probe 401 and returns to the first single-mode fiber 428 side via a reverse light path, and a portion thereof is shifted to the second single-mode fiber 429 side by the optical coupler unit 408 and enters one end of the second single-mode fiber 429 to a photodetector (for example, photodiode 410).

The rotation unit side of the optical rotary joint 403 is driven rotatingly by a radial scanning motor 405 of a rotating drive device 404. Also, the rotation angle of the radial scanning motor 405 is detected by an encoder unit 406. Further, the optical rotary joint 403 includes a linear drive device 407 effecting operation or movement in the insertion direction (axial direction and the opposite direction in the body cavity) of the catheter unit 301 based on the instruction from the signal processing unit 414. The movement in the axial direction is realized by virtue of the operation or control of the linear drive device 407 being based on a control signal from the signal processing unit 414.

It is possible for the radial scanning motor 405 and the linear drive device 407 to be connected detachably or to formed as a single integral or unitary device. Also, the movement in the axial direction by the linear drive device 407 can be realized by way of a ball screw or the like.

On the distal side of the optical coupler unit 408, the second single-mode fiber 429 is provided with a variable mechanism 416 of the light path length for changing the light path length of the reference light. This variable mechanism 416 of the light path length is provided along the path 415 extending distally from the optical coupler 408. The light path between the optical coupler 408 and the variable mechanism 416 constitutes a reference light path.

The variable mechanism 416 of this light path length includes a first light-path length changer for changing, in a relatively high speed manner, a light path length corresponding to an inspection range in the depth direction of the biological tissue, and a second light-path length changer for changing a light path length corresponding to fluctuation of the lengths thereof so as to absorb the fluctuation of the lengths of individual optical probes in case of the use of optical probes that have been exchanged.

Facing the distal tip of the second single-mode fiber 429 and by being mounted on one axis stage 420 together with that distal tip, a grating 419 is arranged through a collimating lens 421 so as to be freely movable in a direction shown by an arrow 423. Also, a galvanomotor 417 rotatable over a relatively small angle is mounted as a first light-path length changer through this grating 419 (diffractive grating) and a corresponding lens 418. This galvanomotor 417 is rotatable in a high-speed manner, in the direction indicated by the arrow 422 direction, by a galvanomotor controller 424.

The galvanomotor 417 is a device for reflecting the light by way of a galvanomotor mirror and it is constructed, by applying an alternate-current drive signal to the galvanomotor which functions as a reference mirror, such that the mirror mounted on the movable portion thereof is capable of being rotated in a relatively high-speed manner.

In other words, a drive signal is applied from the galvanomotor controller 424 with respect to the galvanomotor 417 and it is rotated at a relatively high-speed in the arrow 422 direction by the drive signal, so that the light path length of the reference light is changed in a relatively high-speed manner as much as the light path length corresponding to the inspection range in the depth direction of the biological tissue. One cycle of the change of this light path difference becomes a cycle for obtaining coherent light for one line.

On the other hand, in case of exchanging the optical probe 401, the one axis stage 420 forms a second light-path length changer having a variable range of light path length such that the fluctuation of the light path length of the optical probe can be absorbed. Further, the one axis stage 420 functions as an adjuster for adjusting offset. For example, even in a case in which the distal tip of the optical probe 401 is not closely-attached on the surface of the biological tissue, it is possible, by changing the light path length minutely depending on the one axis stage 420, to set a state of exerting interference from the surface position of the biological tissue.

The light whose light path length is changed by the variable mechanism 416 of the light path length is mixed with the light obtained from the first single-mode fiber 428 side in the optical coupler unit 408 provided along the second single-mode fiber 429 and is light-received by the photodiode 410 as a coherent light.

The coherent light received by the photodiode 410 is converted photoelectrically, is amplified by an amplifier 411 and thereafter, is inputted to a demodulator unit 412. In this demodulator unit 412, there is performed a demodulation process for extracting only a signal component of the coherent light and the output thereof is inputted to an A/D converter 413.

In the A/D converter 413, digital data of one line (coherent light data) are generated by sampling the coherent light signal for 200 points. The sampling frequency has a value obtained by dividing the time period of one scanning of the light path length by 200.

The coherent light data of one line unit which are generated in the A/D converter 413 are inputted to the signal processing unit 414. In this signal processing unit 414, tomographic images at respective positions in the blood vessel are formed by converting the coherent light data in the depth direction to a video signal and are outputted by a predetermined frame rate to an LCD monitor 427.

The signal processing unit 414 is connected with a light path length adjuster control device 426. The signal processing unit 414 carries out position control of the one axis stage 420 through the light path length adjuster control device 426. Also, the signal processing unit 414 is connected with a motor control circuit 425 and controls the rotation drive of the radial scanning motor 405.

Also, the signal processing unit 414 is connected with the galvanomotor controller 424 which controls the scanning of the light path length of the reference mirror (galvanomotor mirror), the galvanomotor controller 424 outputs a drive signal to the signal processing unit 414 and the motor control circuit 425 is synchronized with the galvanomotor controller 424 based on this drive signal.

4. Features of Catheter Connection Detector Unit

Figure 5:
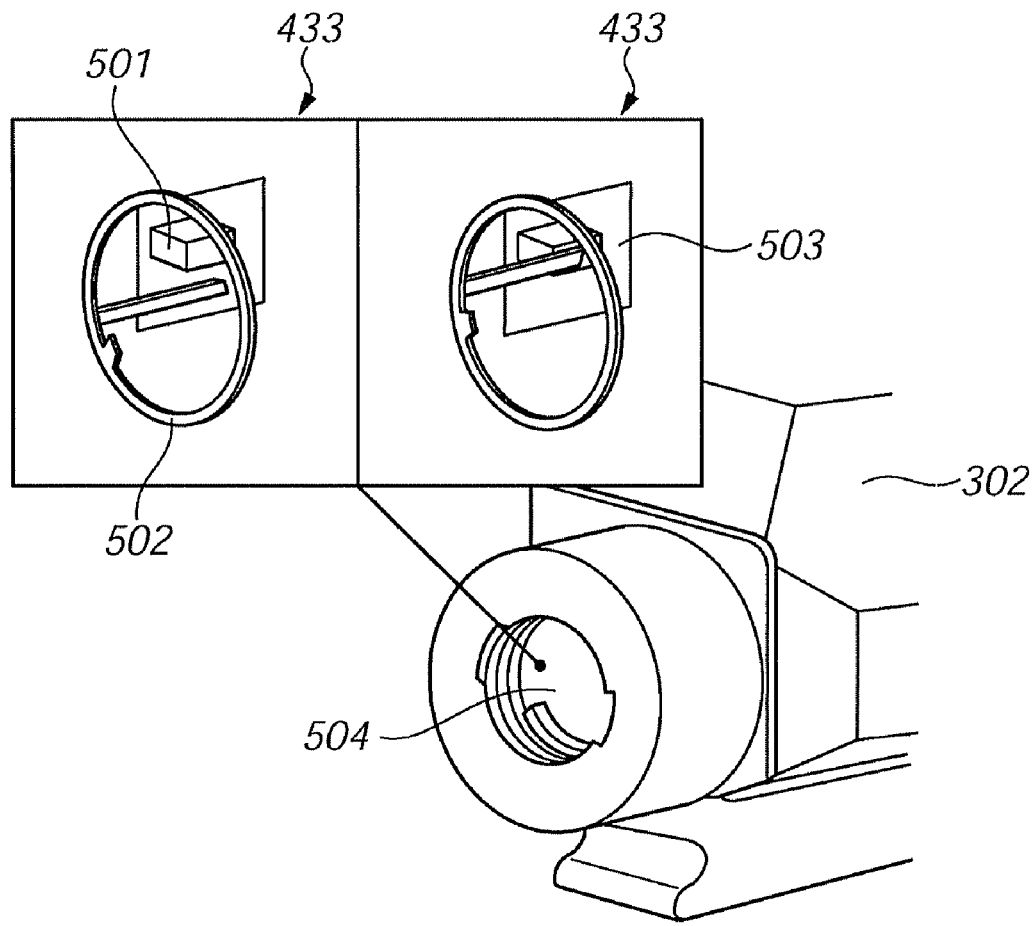
FIGS. 5A-5C are views of a catheter connection detector unit.

Referring to FIGS. 5A-5C, the construction of the catheter connection detector unit 433 will now be described. FIG. 5A shows the distal side of the scanner/pullback unit 302 mounted with the catheter connection detector unit 433. The catheter connection detector unit 433 is mounted at an opening portion 504 on the distal side of the scanner/pullback unit 302.

The optical coherent tomography diagnosis apparatus according to the present exemplified embodiment uses a photo interrupter for the catheter connection detector unit 433. The distal side of the opening portion 504 is provided with a ring 502 as shown in FIG. 5B. In response to the ring 502 rotating when the catheter unit 301 is connected to the scanner/pullback unit 302, a photo interrupter 501 detects this. FIG. 5C shows a state in which the photo interrupter 501 detects the connection of the catheter unit 301 in response to the ring 502 rotating.

5. Features of Shutter Unit and Shutter Control Unit

Figure 6:
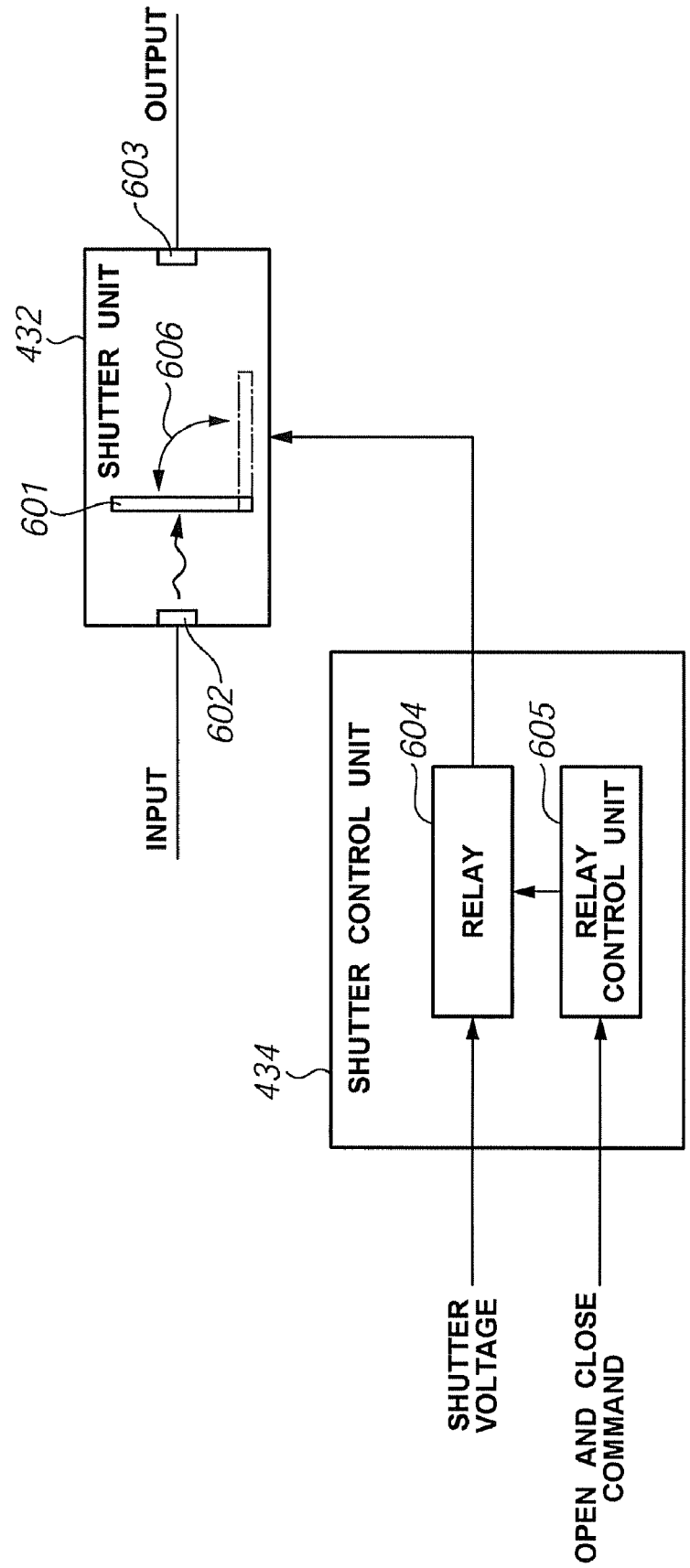
FIG. 6 is a schematic illustration of a shutter unit and a shutter control unit.

FIG. 6 illustrates features of the shutter unit 432 and the shutter control unit 434. As illustrated, the shutter control unit 434 includes a relay control unit 605 and a relay 604. The relay control unit 605 operates the relay 604 depending on an open-command/close-command outputted from the signal processing unit 414 based on a detected result of the catheter connection detector unit 433. The relay 604 is applied with a predetermined voltage from a power supply and the relay 604 is opened and closed under the control of the relay control unit 605.

On the other hand, the shutter unit 432 includes a light incident port 602 which the light of the low coherent light source 409 enters, a light emission port 603 for transmitting the incident light from the light incident port 602 with respect to the optical probe 401, and a shielding body 601 serving as an example of a light shield for shielding the probe (or point of connection of the probe) from the incident light by, for example, cutting off the light path between the light incident port 602 and the light emission port 603. The shutter unit 432 is a light transmission permitting and preventing device which alternatively or selectively permits light at the light incident (inlet) port 602 to exit at the light emission (outlet) port 603 and prevents light at the light incident port 602 from exiting at the light emission port 603.

The shielding body 601 operates freely rotatably in the direction of the arrow 606 between a closed position (shielding position) for shielding the light path on the light path between the light incident port 602 and the light emission port 603 and an open position (non-shielding position) for not shielding the light path. The rotating movement between the close position and the open position according to the shielding body 601 is executed by the open and close operation of the relay 604.

In a case in which the shielding body 601 is in a closed position, the incident light from the light incident port 602 is shielded by the shielding body 601 and therefore, it never happens that light-emission is performed from the light emission port 603.

6. Shutter Opening and Closing Process

Figure 7:
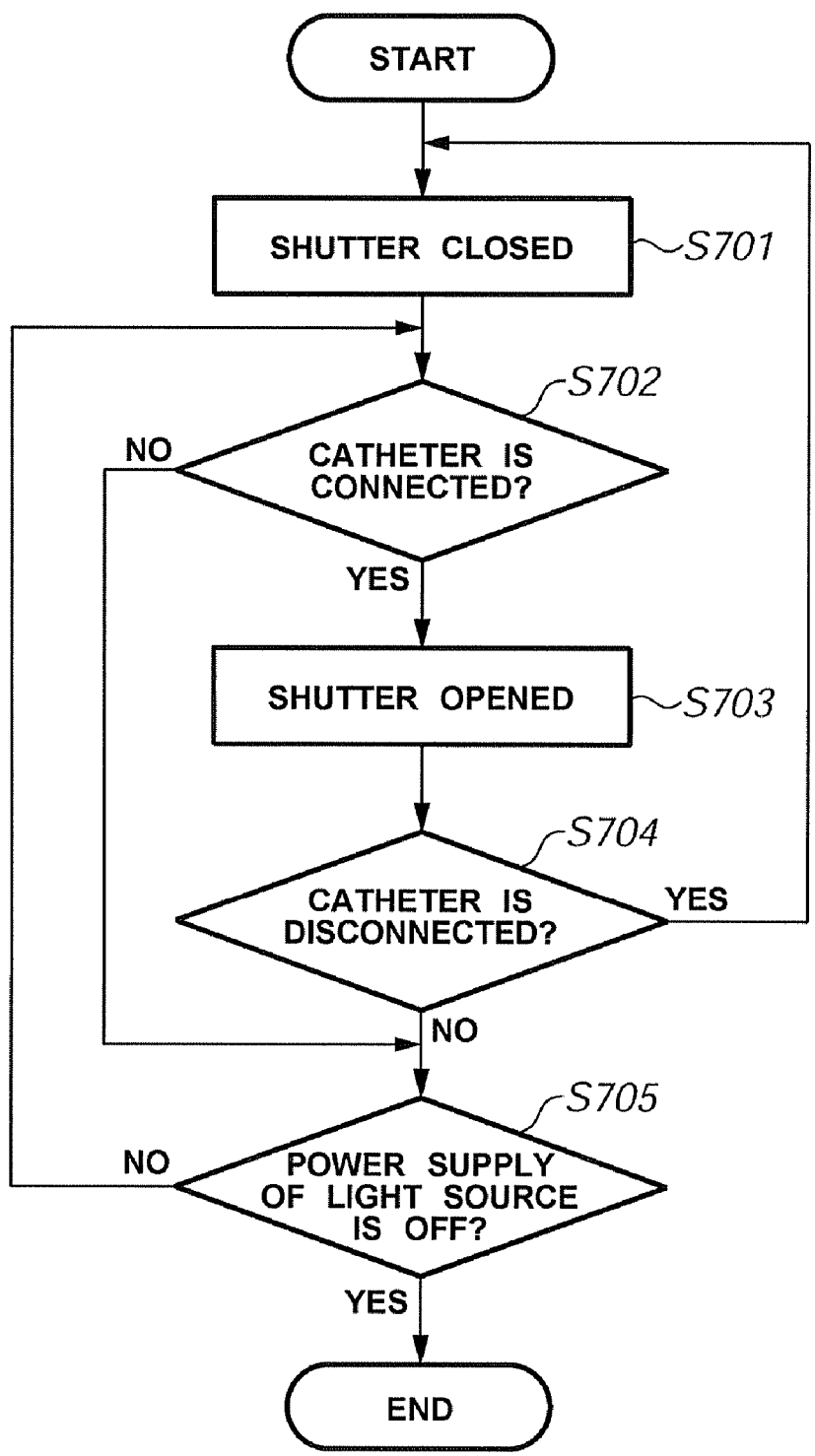
FIG. 7 is a flowchart showing operational aspects of a shutter opening and closing process of the optical coherent tomography diagnosis apparatus shown in FIG. 4.

Referring to FIG. 7, and based on a detected result in the catheter connection detector unit 433, the shutter opening and closing process of the signal processing unit 414 which outputs an open and close command with respect to the shutter control unit 434 is as follows.

When the low coherent light source 409 starts the drive (starts operating), a shutter opening and closing process starts as shown in FIG. 7. In step S701, the shielding body 601 is rotated to the closed position by outputting a close command with respect to the shutter control unit 434. Thus, it does not occur that light is emitted from the operation control unit 303 even in a case in which the low coherent light source 409 is driven.

In step S702, it is judged whether or not the catheter unit 301 is connected based on a detected result from the catheter connection detector unit 433. In a case in which it is judged in step S702 that the catheter unit 301 is not connected, the flow proceeds to step S705 and it is confirmed whether or not the low coherent light source 409 is in a non-drive state, and in a case in which it is in a non-drive state the process ends. On the other hand, in a case in which the low coherent light source 409 is driven, the flow returns to step S702 and the connection of the catheter unit 301 is observed.

In step S702, in a case in which it is judged that the catheter unit 301 is connected, the flow proceeds to step S703 and the shielding body 601 is rotated to an open position by virtue of the shutter control unit 434 outputting an open command. Thus, the measuring light is emitted from the catheter unit 301. In other words, when the diagnosis preparation is completed in which the catheter unit 301 is connected to the scanner/pullback unit 302, a state is reached in which the measuring light is emitted.

In step S704, it is judged whether or not the catheter unit 301 has become disconnected state. In a case in which it is judged that the catheter unit 301 has not become disconnected, the flow proceeds to step S705 and it is confirmed whether or not the low coherent light source 409 is in a non-drive state, and in a case in which the low coherent light source 409 is driven (NO in S705), the flow returns to step S702.

On the other hand, in a case in which it is judged that the catheter unit 301 is in a disconnection state, the flow returns to step S701 and the shielding body 601 is rotated to the closed position through the output of a close command with respect to the shutter control unit 434.

In this manner, a shutter opening and closing process is executed in the signal processing unit 414 during a period when the low coherent light source 409 is driven, and the measuring light is emitted only during a period when the catheter unit 301 is connected. When the catheter unit 301 is in a disconnection state, the shutter is closed so as not to emit the measuring light.

As clear from the explanation above, according to the optical coherent tomography diagnosis apparatus relating to the present exemplified embodiment, the measuring light will never be emitted to the outside in a situation in which the catheter unit is not connected, even in a case in which the low coherent light source is driven. It thus becomes possible to avoid reception of the measuring light before and after the diagnosis. Also, the light source is not stopped and so the diagnosis apparatus can be used at once (immediately) after the connection thereof or as desired.

Second Exemplified Embodiment

The first exemplified embodiment mentioned above employs a construction in which the measuring light is shielded by rotating the shutter to a closed position, that is by moving the shielding body into the light path of the measuring light to block the light path. However, the apparatus here is not limited in this regard, as it is also possible to employ a construction in which the light-emission of the measuring light to the outside is not permitted, for example by deviating or redirecting the light path of the measuring light to the direction of the shielding body.

1. Features of Optical Coherent Tomography Diagnosis Apparatus

Figure 8:
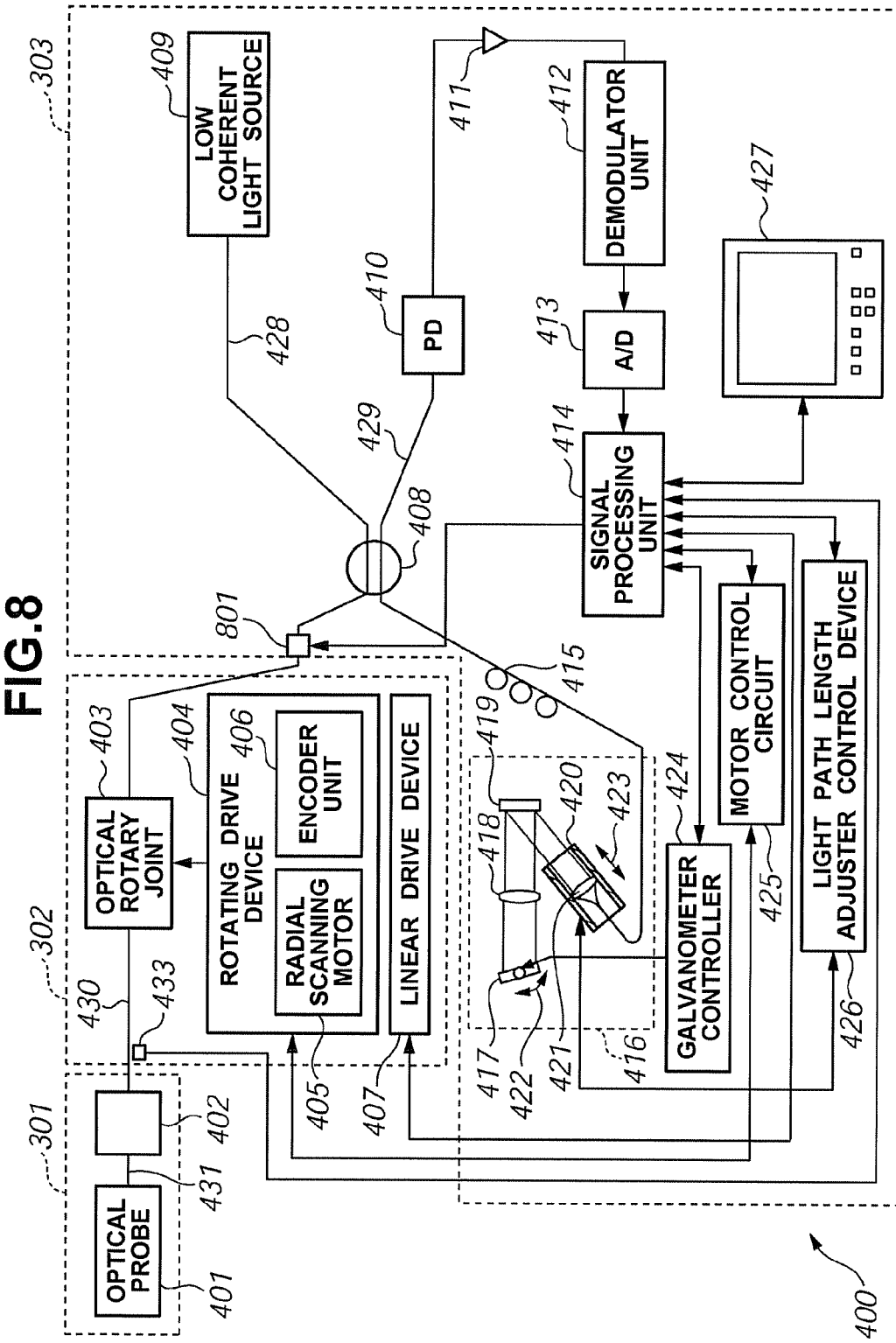
FIG. 8 is a schematic illustration of aspects of an optical coherent tomography diagnosis apparatus according to a second exemplified embodiment disclosed here.

FIG. 8 is a schematic illustration of an optical coherent tomography diagnosis apparatus 800 according to a second exemplified embodiment. This embodiment differs with respect to the embodiment of the optical coherent tomography diagnosis apparatus 300 described above in that a frequency shifter unit 801 is utilized instead of the shutter unit 432 and the apparatus is constructed such that an RF signal from the signal processing unit 414 is inputted to the frequency shifter unit 801 directly based on a detected result of the catheter connection detector unit 433.

2. Features of Frequency Shifter Unit

Figure 9:
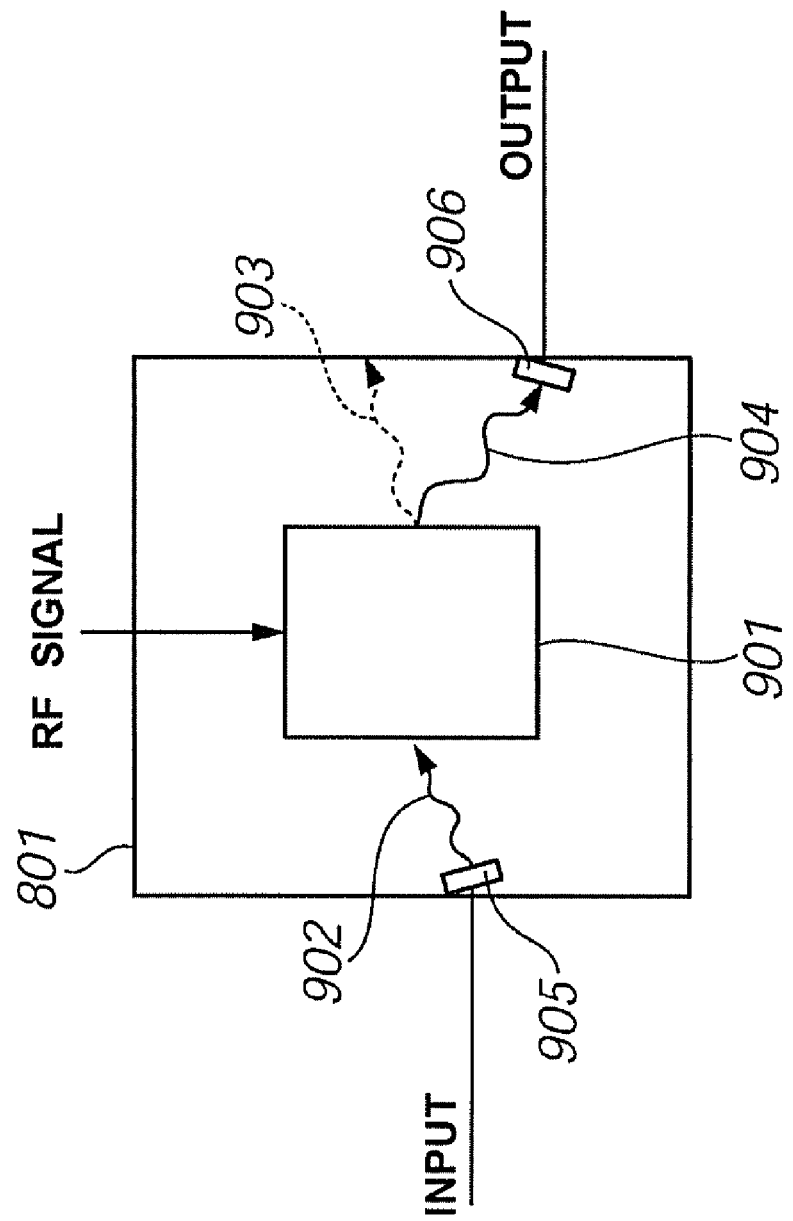
FIG. 9 is a view of a frequency shifter unit.

Referring to FIG. 9, the frequency shifter unit 801 used in this embodiment of the optical coherent tomography diagnosis apparatus 800 includes a light incident (inlet) port 905 which the light from the low coherent light source 409 enters, an acoustooptical device 901 for shifting the light frequency by diffracting an incident light 902 from the light incident port 905 (serving as another example of a light shield that shields incident light from the probe or a point of connection for the probe), and a light emission (outlet) port 906 for emitting a light 904 whose frequency is shifted. The frequency shifter unit 801 is a light transmission permitting and preventing device which alternatively or selectively permits incident light at the light incident port 905 to exit at the light emission port 906 and prevents light at the light incident port 905 from exiting at the light emission port 906.

In the frequency shifter unit 801, when an RF signal is inputted from the signal processing unit 414, the incident light 902 entering the light incident port 905 is diffracted in the acoustooptical device 901 and light-emission is carried out from the light emission port 906. On the contrary, in a case in which the RF signal is not inputted from the signal processing unit 414, diffraction of the light does not occur in the acoustooptical device 901, so that the incident light from the light incident port 905 is not directed toward, or in the direction of, the light emission port 906, but rather is reflected in the housing constituting the frequency shifter unit 801 as indicated by the light path identified as 903 in FIG. 9. Therefore, the light-emission from the light emission port 906 does not occur.

In this manner, the light path between the light incident port 905 and the light emission port 906 is controlled in the frequency shifter unit 801 depending on the presence or absence of the RF signal. In a situation in which it is not desired for the light to be emitted from the light emission port 906, the housing of the frequency shifter unit 801 functions as a shielding body.

3. Control Process of Frequency Shifter Unit

Figure 10:
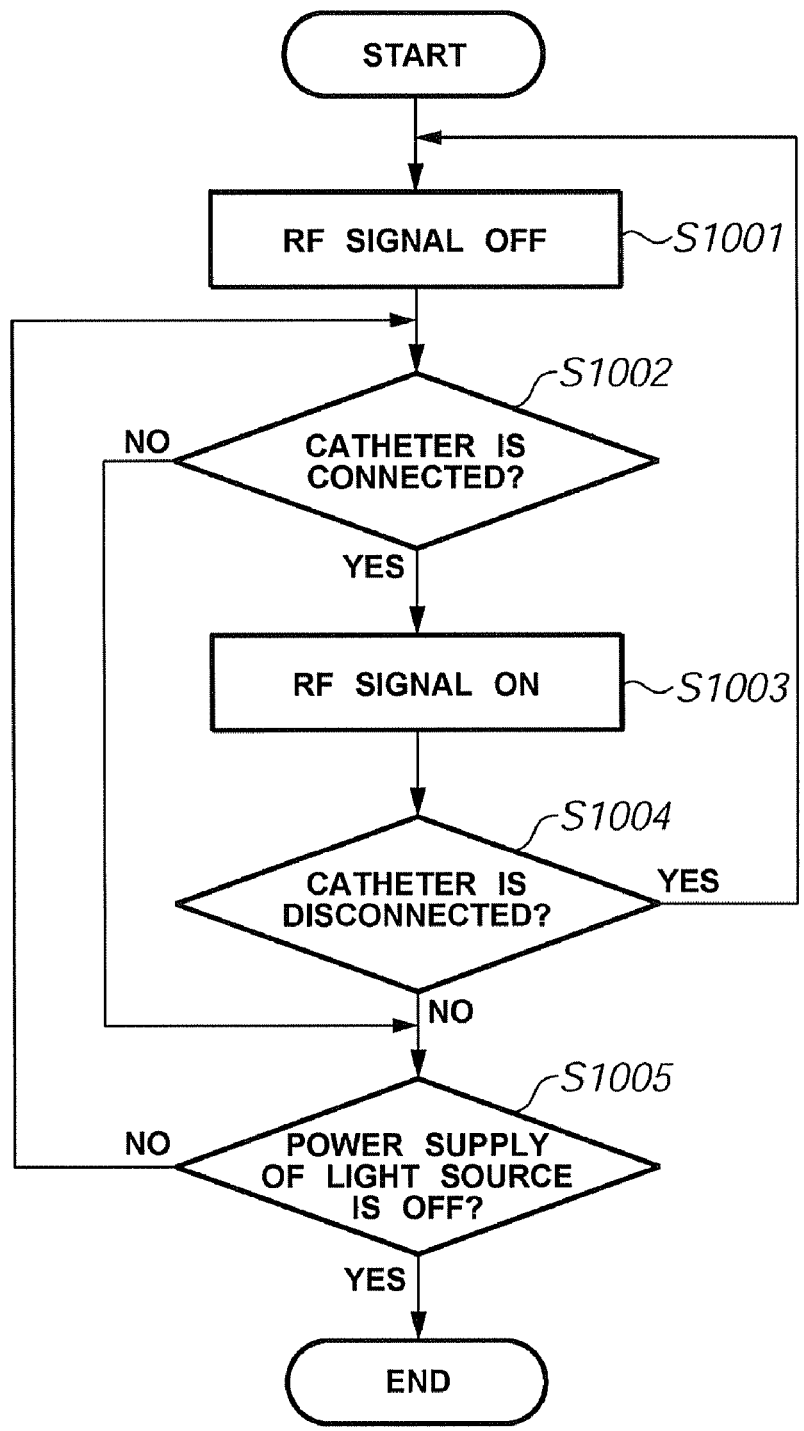
FIG. 10 is a flowchart showing operational aspects of a control process of the frequency shifter unit in the optical coherent tomography diagnosis apparatus shown in FIG. 8.

Referring to FIG. 10, and based on a detected result in the catheter connection detector unit 433, the control process of the signal processing unit 414 which controls the RF signal outputted with respect to the frequency shifter unit 801 is discussed next. When the low coherent light source 409 starts driving operation (i.e., is being operated), the control process shown in FIG. 10 is initiated. In step S1001, the RF signal outputted by the frequency shifter unit 801 is turned OFF. Thus, even in a case in which the low coherent light source 409 starts being driven, it never happens that the light is emitted from the operation control unit 303.

In step S1002, it is judged whether or not the catheter unit 301 is connected based on a detected result from the catheter connection detector unit 433. If it is judged in step S1002 that the catheter unit 301 is not connected, the flow proceeds to step S1005 and it is confirmed whether or not the low coherent light source 409 is in a non-drive state. If the low coherent light source 409 is in a non-drive state, the process ends. On the other hand, in a case in which the low coherent light source 409 is in a driven state, the flow returns to step S1002 and the connection of the catheter unit 301 is confirmed.

In step S1002, in a case in which it is judged that the catheter unit 301 is connected, the flow proceeds to step S1003 and the incident light from the light incident port 905 is diffracted, and the light is emitted from the light emission port 906 by outputting an RF signal with respect to the frequency shifter unit 801. Thus, the measuring light is emitted from the catheter unit 301. In other words, when the diagnosis preparation is completed in which the catheter unit 301 is connected to the scanner/pullback unit 302, the measuring light is emitted.

In step S1004, it is judged whether or not the catheter unit 301 becomes disconnected. In a case in which it is judged that the catheter unit 301 does not become disconnected, the flow proceeds to step S1005 and it is confirmed whether or not the low coherent light source 409 is not in a non-drive state. In a situation in which the low coherent light source 409 is driven (NO in S1005), the flow returns to step S1002.

On the other hand, when it is judged that the catheter unit 301 is in a disconnection state, the flow returns to step S1001 and the RF signal outputted with respect to frequency shifter unit 801 is turned OFF.

In this manner, a control process of the frequency shifter unit 801 is executed in the signal processing unit 414 during a period when the low coherent light source 409 is driven and the measuring light is emitted only during a period when the catheter unit 301 is connected, and when the catheter unit 301 is in a disconnection state, the frequency shifter unit 801 is controlled so as not to emit the measuring light.

As clear from the explanation above, according to the optical coherent tomography diagnosis apparatus relating to the present exemplified embodiment, the measuring light will never be emitted to the outside in a case in which the catheter unit is not connected, even in a case in which the low coherent light source is driven. Also, it is possible to avoid reception of the measuring light before and after the diagnosis.

This embodiment of the apparatus is constructed such that the frequency shifter unit for adjusting the emitted measuring light is commonly used to control the emission of the measuring light to obtain a collateral effect that the apparatus cost can be reduced as compared with an arrangement such as the first embodiment described above in which a shutter unit and a shutter control unit are provided separately.

Third Exemplified Embodiment

The first and the second embodiments described above by way of examples employ a construction in which the measuring light is emitted during a period when the catheter unit is connected. However, the apparatus is not limited in that regard. Since the optical probe does not rotate during the period from the time when the catheter unit is connected to the time when the measurement starts after the catheter unit is inserted into blood vessel, the emitted measuring light continues to illuminate a specified direction. As a result thereof, it is considered that some sort of influence is also exerted on the biological tissue.

In the present exemplified embodiment, the open and close of the shutter unit is controlled under a condition in which it is connected with the catheter unit and also the optical probe is rotated. Hereinafter, details will be explained with respect to the optical coherent tomography diagnosis apparatus according to a further exemplified embodiment.

1. Features of Optical Coherent Tomography Diagnosis Apparatus

The optical coherent tomography diagnosis apparatus according to the present exemplified embodiment is basically the same as that of the embodiment shown in FIG. 4 and so a detailed explanation is not repeated. In this embodiment, the presence or absence of rotation of the optical probe 401 is judged by the signal processing unit 414 which receives the output of the encoder unit 406 through the motor control circuit 425.

2. Shutter Opening and Closing Process

Figure 11:
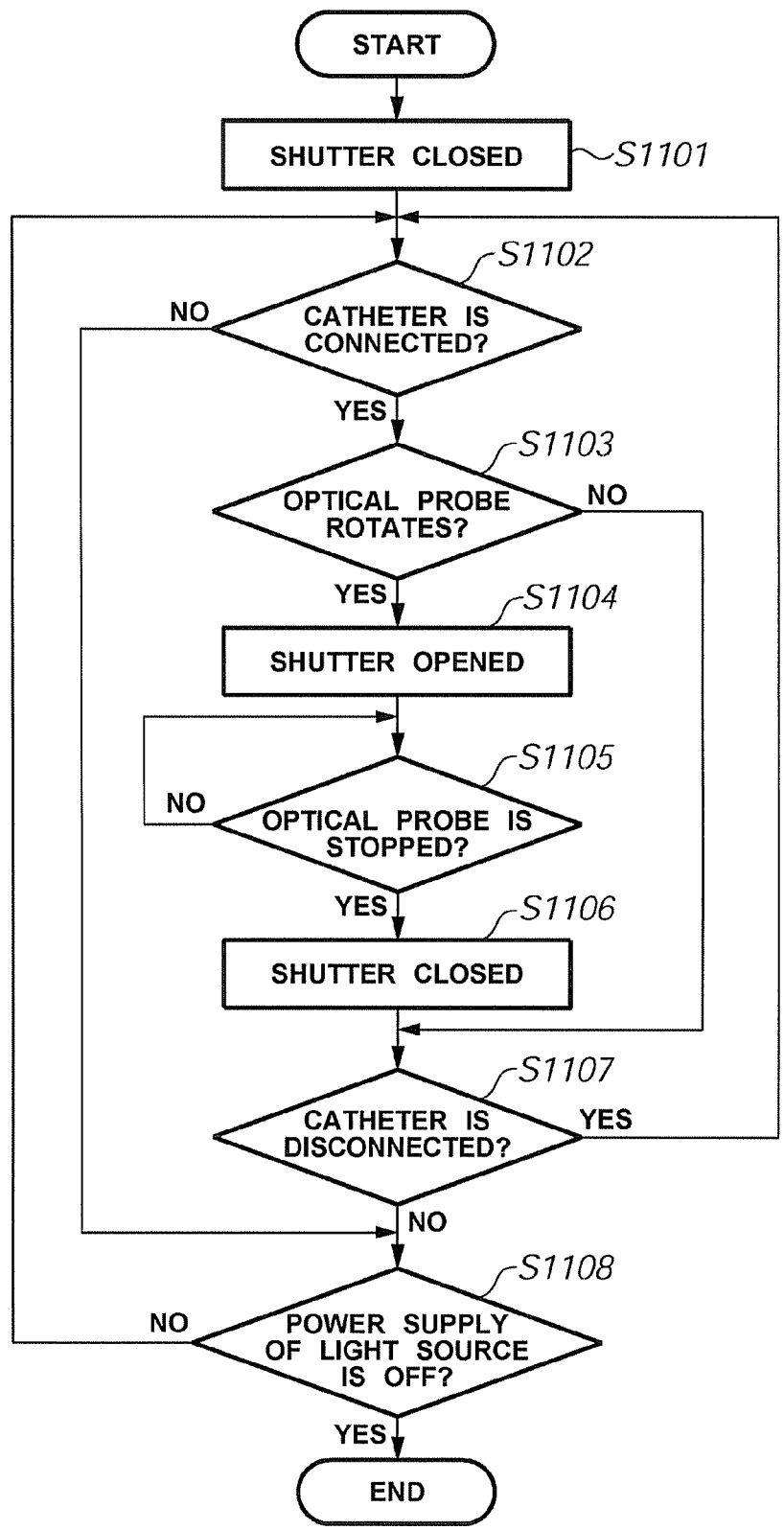
FIG. 11 is a flowchart showing operational aspects of a shutter opening and closing process in the optical coherent tomography diagnosis apparatus according to a third exemplified embodiment disclosed here.

FIG. 11 is a flowchart showing the shutter opening and closing process in the optical coherent tomography diagnosis apparatus according to the present exemplified embodiment.

When the low coherent light source 409 starts the drive (begins operating), a shutter opening and closing process starts as shown in FIG. 11. In step S1101, the shielding body 601 is rotated to the close position by outputting a close command from the shutter control unit 434. Thus, a situation does not arise in which the light is emitted from the operation control unit 303 even in a case in which the low coherent light source 409 starts operating.

In step S1102, it is judged whether or not the catheter unit 301 is connected based on a detected result from the catheter connection detector unit 433. In a case in which it is judged in step S1102 that the catheter unit 301 is not connected, the flow proceeds to step S1108 and it is confirmed whether or not the low coherent light source 409 is in a non-drive state, and in a case in which it is in a non-drive state, the process is ended. On the other hand, if the low coherent light source 409 is being driven (is operating), the flow returns to step S1102 and the connection of the catheter unit 301 is observed.

On the other hand, when it is judged in step S1102 that the catheter unit 301 is connected, the flow proceeds to step S1103 and it is judged based on the output of the encoder unit 406 whether or not the optical probe 401 is rotating. When it is judged in step S1103 that the optical probe 401 does not rotate, the flow proceeds to step S1107 and it is determined whether or not the catheter unit 301 is disconnected (becomes in a disconnection state). If it is judged that the catheter unit 301 does not become in a disconnection state, the flow proceeds to step S1108 and drive/non-drive of the low coherent light source 409 is confirmed, and thereafter the flow returns to step S1102.

On the other hand, in a case in which it is judged in step S1103 that the optical probe 401 is rotating, the flow proceeds to step S1104 and the shielding body 601 is rotated to the open position by outputting an open command with respect to the shutter control unit 434. Thus, the measuring light is emitted from the catheter unit 301. In other words, the catheter unit 301 is in a state in which the catheter unit 301 is connected to the scanner/pullback unit 302 and the measuring light is to be emitted when the rotation of the optical probe is started.

In step S1105, it is judged whether or not the rotation of the optical probe 401 is stopped based on the output of the encoder unit 406. In step S1105, in a case in which it is judged that the optical probe 401 is not rotating, the flow proceeds to step S1106 and the shielding body 601 is rotated to the closed position by the output of a close command signal from the shutter control unit 434.

In step S1107, it is judged whether or not the catheter unit 301 becomes in a disconnection state. In a case in which it is judged in step S1107 that the catheter unit 301 becomes disconnected, the flow returns to step S1102 and it is observed whether or not the catheter unit 301 is connected.

On the other hand, in a case in which it is judged in step S1107 that the catheter unit 301 is not disconnected, the drive/non-drive of the low coherent light source 409 is confirmed in step S1108 and thereafter, the flow returns to step S1102.

In this manner, in the signal processing unit 414, a shutter opening and closing process is executed during a period when the low coherent light source 409 is driven (operated), and the measuring light is emitted only during a period when the catheter unit 301 is connected and also the optical probe rotates. The shutter is closed to not emit the measuring light in a case in which the optical probe does not rotate although the catheter unit 301 is connected or in a case in which the catheter unit 301 is not connected.

In this optical coherent tomography diagnosis apparatus relating to the present exemplified embodiment, the measuring light will never be emitted if it is not in a state in which the catheter unit is connected and also the optical probe rotates, even in a case in which the low coherent light source is driven (operates). It is thus possible to avoid receiving the measuring light before and after the diagnosis.

Fourth Exemplified Embodiment

The third exemplified embodiment discussed above employs a construction in which the shutter is opened and the measuring light is emitted in a case in which the catheter unit is connected and the optical probe is in a rotating condition. However, the apparatus is not limited in this regard, and it is possible, similar to the second exemplified embodiment, to employ a construction in which the operation of the frequency shifter is controlled under the state thereof.

1. Features of Optical Coherent Tomography Diagnosis Apparatus

The features of the optical coherent tomography diagnosis apparatus according to the present exemplified embodiment is basically the same as that shown in FIG. 8 and so an explanation is not repeated. In the apparatus here, the presence or absence of the rotation of the optical probe 401 is judged by the signal processing unit 414 which receives the output of the encoder unit 406 through the motor control circuit 425.

2. Control Process of Frequency Shifter

Figure 12:
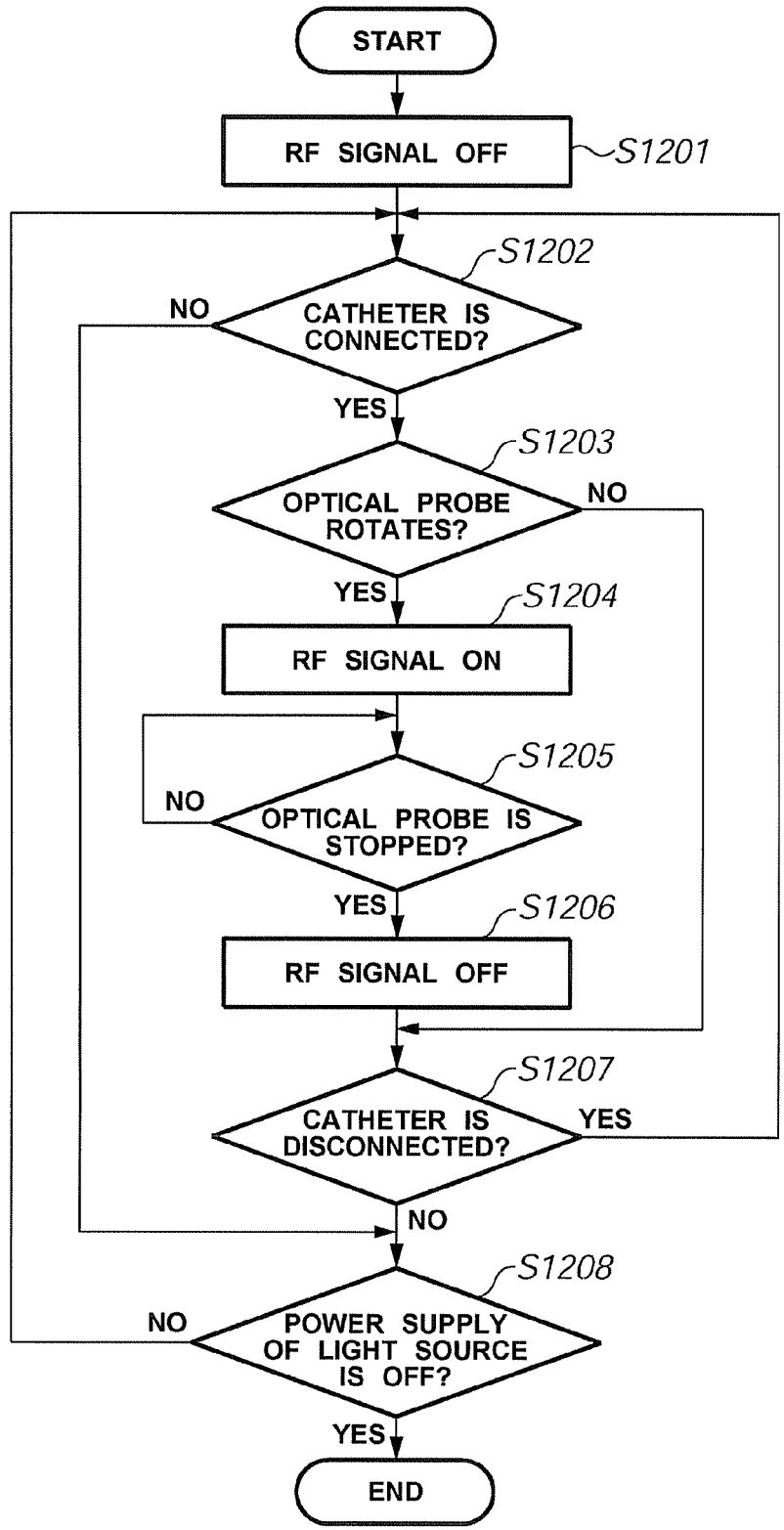
FIG. 12 is a flowchart showing operational aspects of a control process of the frequency shifter unit in the optical coherent tomography diagnosis apparatus according to a fourth exemplified embodiment disclosed here.

FIG. 12 illustrates the control process of the frequency shifter unit 801 in the optical coherent tomography diagnosis apparatus according to the present exemplified embodiment. When the low coherent light source 409 starts to be driven (operated), a control process shown in FIG. 12 will start. In step S1201, the RF signal outputted with respect to the frequency shifter unit 801 is turned OFF. Thus, even in a case in which the low coherent light source 409 starts being driven, it never happens that the light will be emitted from the operation control unit 303.

In step S1202, it is judged whether or not the catheter unit 301 is connected based on a detected result from the catheter connection detector unit 433. In a case in which it is judged in step S1202 that the catheter unit 301 is not connected, the flow proceeds to step S1208 and it is confirmed whether or not the low coherent light source 409 is in a non-drive state, and in a case in which it is in a non-drive state, the process is ended. On the other hand, in a case in which the low coherent light source 409 is driven (NO at step S1208), the flow returns to step S1202 and the connection of the catheter unit 301 is observed.

In step S1202, in a case in which it is judged that the catheter unit 301 is connected, the flow proceeds to step S1203 and it is judged based on the output of the encoder unit 406 whether or not the optical probe 401 rotates. In step S1203, in a case in which it is judged that the optical probe 401 does not rotate, the flow proceeds to step S1207 and it is judged whether or not the catheter unit 301 becomes in a disconnection state. In a case in which it is judged that the catheter unit 301 is not in a disconnection state, the flow proceeds to step S1208 and drive/non-drive nature of the low coherent light source 409 is determined or confirmed. If NO in step S1208, the flow returns to step S1202.

On the other hand, in a case in which it is judged in step S1203 that the optical probe 401 is rotating, the flow proceeds to step S1204 and the incident light from the light incident port 905 is diffracted, and the light is emitted from the light emission port 906 by outputting an RF signal from the frequency shifter unit 801. Thus, the measuring light is emitted from the catheter unit 301. In other words, a state exists in which the catheter unit 301 is connected to the scanner/pullback unit 302 and the measuring light is to be emitted when the rotation of the optical probe is started.

In step S1205, it is judged whether or not the rotation of the optical probe 401 is stopped based on the output of the encoder unit 406. When it is judged in step S1205 that the optical probe 401 is not rotating (is stopped), the flow proceeds to step S1206 and the RF signal outputted with respect to frequency shifter unit 801 is turned OFF.

In step S1207, it is judged whether or not the catheter unit 301 becomes the disconnection state. In a case in which it is judged in step S1207 that the catheter unit 301 is disconnected, the flow returns to step S1202 and it is observed whether or not the catheter unit 301 is connected.

On the other hand, in a case in which it is judged in step S1207 that the catheter unit 301 does not become the disconnection state, the drive/non-drive of the low coherent light source 409 is confirmed in step S1208 and thereafter, in the case of NO in step S1208, the flow returns to step S1202.

In this manner, a control process of the frequency shifter unit 801 is executed in the signal processing unit 414 during a period when the low coherent light source 409 is driven (is operating) and the measuring light is emitted only during a period when the catheter unit 301 is connected and also the optical probe rotates, and the frequency shifter unit 801 is controlled so as not to emit the measuring light in a case in which the optical probe does not rotate although the catheter unit 301 is connected or in a case in which the catheter unit 301 is not connected.

According to the optical coherent tomography diagnosis apparatus of this exemplified embodiment, the measuring light will never be emitted to the outside if the apparatus is not in a state in which the catheter unit is connected and also the optical probe rotates even in a case in which the low coherent light source is driven, and it becomes possible to avoid reception of the measuring light before and after the diagnosis.

Fifth Exemplified Embodiment

Considering the aspect of the third and the fourth exemplified embodiments discussed above that there is a possibility for the emitted measuring light to illuminate a specified region for a long time period until the optical probe starts the rotation in a case in which the catheter is connected, there is employed a construction in which the measuring light is to be controlled such that it will never be emitted to the outside.

However, the apparatus here is not limited in this regard. For example, based on a fact that there is virtually no influence on a human body if an illumination occurs for a short time period, even if it occurs when the catheter is connected and until the optical probe rotates, it is also possible to perform a shutter opening and closing process or a control process of the frequency shifter unit by limiting the time period for emitting the measuring light.

Figure 13:
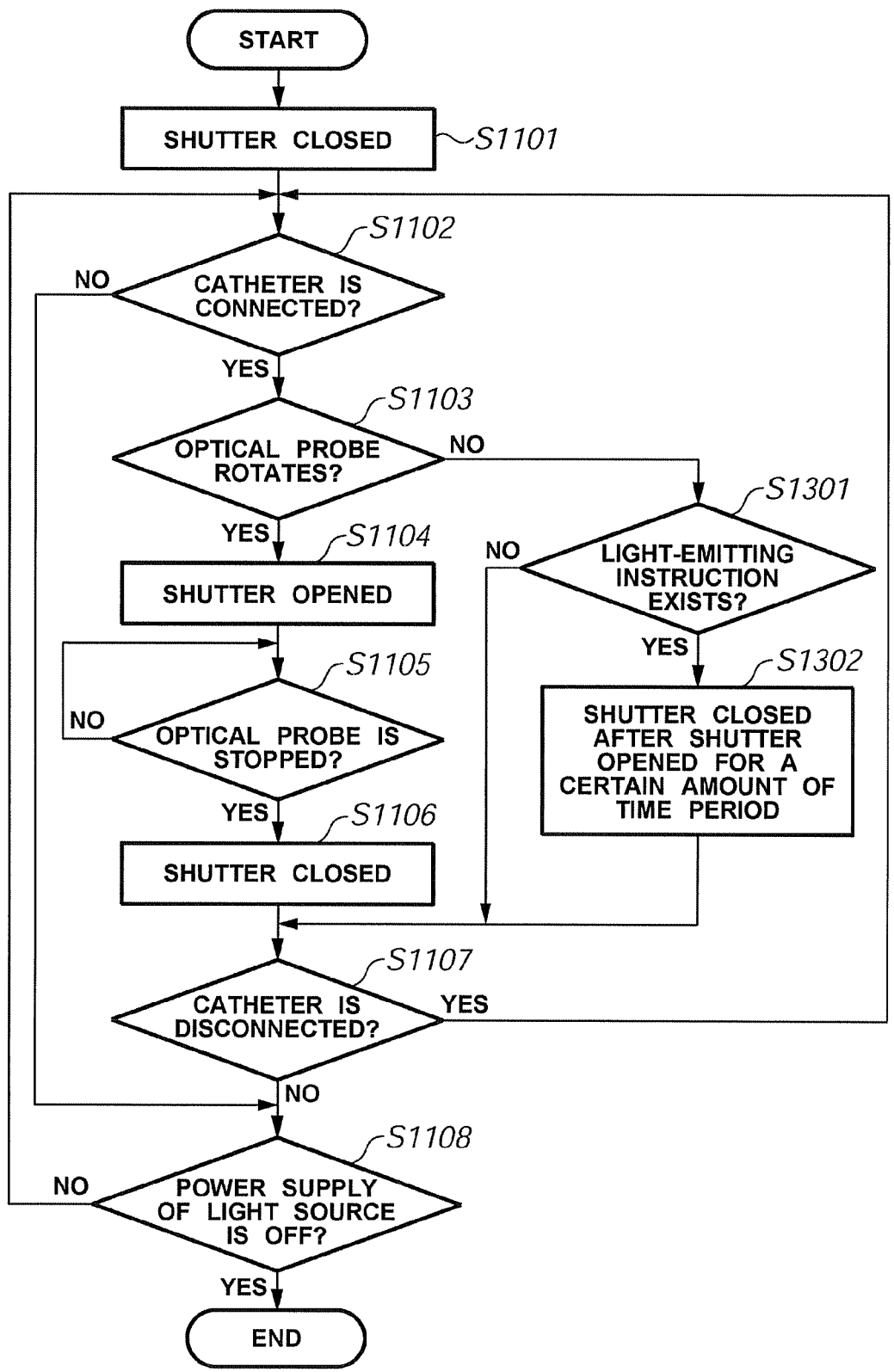
FIG. 13 is a flowchart showing operational aspects of a control process of a shutter opening and closing process in the optical coherent tomography diagnosis apparatus according to a fifth exemplified embodiment disclosed here.

FIG. 13 illustrates a shutter opening and closing process in the optical coherent tomography diagnosis apparatus according to another exemplified embodiment. Aspects of the process shown in FIG. 13 that are similar to those in FIG. 11 are designated by the same reference numerals and a detailed discussion of such aspects is not repeated. The description below primarily discusses aspects of the process different from those in the flowchart of FIG. 11.

In a case in which it is judged in step S1103 that the optical probe 401 does not rotate, the flow proceeds to step S1301. In step S1301, it is judged whether or not the signal processing unit 414 accepted a light-emitting instruction. The light-emitting instruction in a state in which the optical probe 401 is non-rotational means, for example, a situation in which the operator inputs a light-emitting instruction manually and the signal processing unit 414 recognizes this or the like.

In step S1301, in a case in which it is judged that there is no light-emitting instruction, the flow proceeds to step S1107. On the other hand, in a case in which it is judged in step S1301 that there is a light-emitting instruction, the flow proceeds to step S1302 and the shielding body 601 is rotated to the open position by outputting an open command from the shutter control unit 434. Further, after a predetermined time period, the shielding body 601 is rotated to the closed position by outputting a close command from the shutter control unit 434.

Thus, in a state in which the catheter unit 301 is connected, it becomes possible, even in a case in which the optical probe 401 does not rotate, to emit the measuring light limited by a predetermined time period under an instruction of the operator.

In the present exemplified embodiment, a situation was explained in which the shutter unit 432 is controlled, but it is possible to execute a similar process also with respect to a case in which the frequency shifter unit 801 is controlled.

Sixth Exemplified Embodiment

In the first and the second exemplified embodiments described above, a construction is employed in which the measuring light is controlled so as not to be emitted until the catheter is connected and the measuring light is controlled so as to be emitted after the catheter is connected. The third and fourth exemplified embodiments employ a construction in which the measuring light is further controlled so as not to be emitted until the optical probe rotates, even if the catheter is connected and the measuring light is controlled, so as to be emitted only when the optical probe is in a rotation state. However, the apparatus covered here are not limited in this regard.

Generally, the measuring light emitted from the distal portion of the scanner and pull-back unit 302 in a state in which the catheter is disconnected will scatter, so that there are a lot of situations in which no problem occurs even if it is illuminated on a human body for a long time period. On the contrary, the light emitted from the distal tip of the optical probe by connecting the catheter is focused by a lens, so that there is a rather significant possibility that some sort of influence occurs in a case in which it is illuminated on a human body for a relatively long time period.

Consequently, in the present exemplified embodiment, the measuring light is emitted until the catheter is connected and the measuring light is controlled so as not to be emitted during the period from the time when the catheter is connected to the time when the optical probe starts the rotation. The description below will explain a shutter opening and closing process and also a control process of the frequency shifter according to the present exemplified embodiment.

Figure 14:
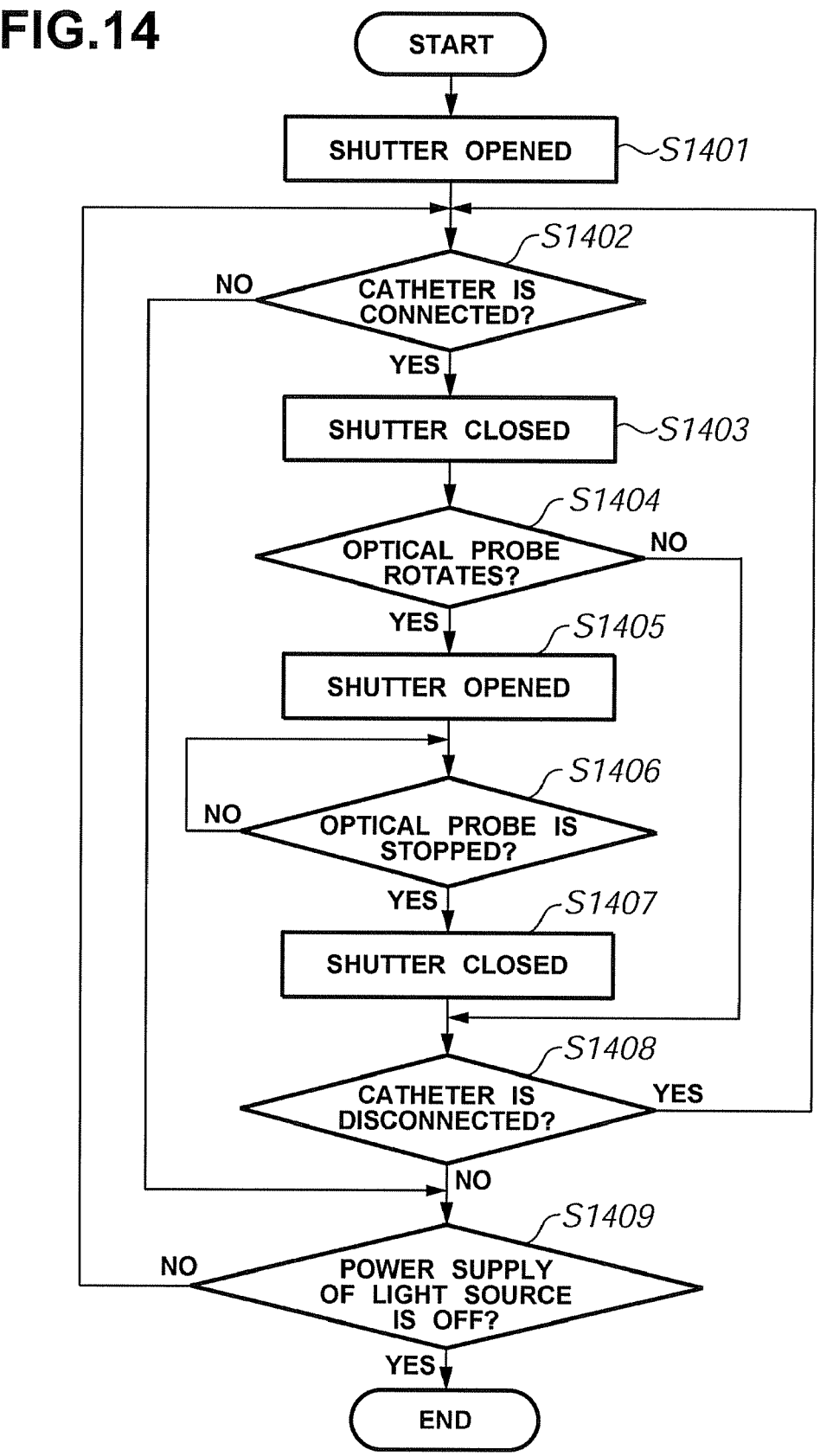
FIG. 14 is a flowchart showing operational aspects of a control process of a shutter opening and closing process in the optical coherent tomography diagnosis apparatus according to a sixth exemplified embodiment disclosed here.

FIG. 14 depicts a shutter opening and closing process in the optical coherent tomography diagnosis apparatus according to the present exemplified embodiment. When the low coherent light source 409 starts the drive (operation), a shutter opening and closing process shown in FIG. 14 starts. In step S1401, the shielding body 601 is rotated to the open position by outputting an open command signal from the shutter control unit 434.

In step S1402, it is judged whether or not the catheter unit 301 is connected based on a detected result from the catheter connection detector unit 433. In a case in which it is judged in step S1402 that the catheter unit 301 is not connected, the flow proceeds to step S1409 and it is confirmed whether or not the low coherent light source 409 is in a non-drive state, and in a case in which it is in a non-drive state, the process is ended. On the other hand, in a case in which the low coherent light source 409 is driven, the flow returns to step S1402 and the connection of the catheter unit 301 is observed.

In step S1402, in a case in which it is judged that the catheter unit 301 is connected, the flow proceeds to step S1403 and the shielding body 601 is rotated to the closed position by outputting a close command with respect to the shutter control unit 434. Thus, it never happens that the measuring light will be emitted after the catheter unit 301 is connected until the optical probe 401 rotates.

In step S1404, based on the output of the encoder unit 406, it is judged whether or not the optical probe 401 rotates. In step S1404, in a case in which it is judged that the optical probe 401 does not rotate, the flow proceeds to step S1408 and it is judged whether or not the catheter unit 301 becomes a disconnection state. In a case in which it is judged that the catheter unit 301 is not in a disconnected state, the flow proceeds to step S1409 and drive/non-drive of the low coherent light source 409 is assessed. If the result of step S1409 is NO, the flow returns to step S1402.

On the other hand, in a case in which it is judged in step S1404 that the optical probe 401 is rotating, the flow proceeds to step S1405 and the shielding body 601 is rotated to the open position by outputting an open command from the shutter control unit 434. Thus, the measuring light is emitted from the catheter unit 301. In other words, a state occurs in which the catheter unit 301 is connected to the scanner/pullback unit 302 and the measuring light is emitted when the rotation of the optical probe is started.

In step S1406, based on the output of the encoder unit 406, it is judged whether or not the rotation of the optical probe 401 is stopped. In step S1406, when it is judged that the optical probe 401 does not rotate, the flow proceeds to step S1407 and the shielding body 601 is rotated to the closed position by outputting a close command with respect to the shutter control unit 434.

In step S1408, it is judged whether or not the catheter unit 301 is in a disconnection state. In a case in which it is judged in step S1408 that the catheter unit 301 is in a disconnection state, the flow returns to step S1401, an open command is outputted with respect to the shutter control unit 434, and thereafter it is observed whether or not the catheter unit 301 is connected.

On the other hand, in a case in which it is judged in step S1408 that the catheter unit 301 is not in a disconnection state, the drive/non-drive of the low coherent light source 409 is confirmed in step S1409 and thereafter, the flow returns to step S1402.

In this manner, in the signal processing unit 414, a shutter opening and closing process is executed during a period when the low coherent light source 409 is driven (operated) and the measuring light is emitted only during a period when the catheter unit 301 is disconnected and during a period the catheter unit 301 is connected and also the optical probe rotates, and the shutter is to be closed so as not to emit the measuring light in a case in which the optical probe does not rotate although the catheter unit 301 is connected.

According to the optical coherent tomography diagnosis apparatus relating to the present exemplified embodiment, the measuring light will never be emitted if the apparatus is not in a state in which the catheter unit is disconnected or in a state in which the catheter unit is connected and also the optical probe rotates, even in a case in which the low coherent light source is driven. It thus becomes possible to avoid reception of the measuring light before and after the diagnosis.

The description associated with the present exemplified embodiment explains a situation in which the shutter unit 432 is controlled, but it is possible to execute a similar process also in case of controlling the frequency shifter unit 801.

Seventh Exemplified Embodiment

The first to the sixth exemplified embodiments discussed above employ a construction in which a material not passing through the measuring light is used as a shielding body, but the apparatus at issue here is not limited in this regard. For example, it may be a material which can be reduced for the amount of the passing-through light until a level which has no-problem even if it receives light continuously for a long time period.

Also, the first to the sixth exemplified embodiments described above employ a construction in which the shutter opening and closing process or the control process of the frequency shifter is executed based on the output from the encoder unit detecting the rotation of the optical probe. However, the apparatus at issue here is not limited in this regard, and it is also possible to employ a constitution in which the control of the shutter opening and closing process or the process of the frequency shifter is executed based on the rotation command of the optical probe. Alternatively, it is also possible to employ a construction in which a sensor for detecting the rotation of the optical probe is provided separately from the encoder unit and the shutter opening and closing process or the control process of the frequency shifter is executed based on the output of the sensor thereof.

Eighth Exemplified Embodiment

The first to the seventh exemplified embodiments mentioned above are explained with respect to a situation in which the diagnosis apparatus is applied to an optical coherent tomography diagnosis apparatus, but the apparatus here is not limited by this case and it is also possible to apply the diagnosis apparatus to a wavelength-sweeping optical coherent tomography diagnosis apparatus. The description below will describe application of aspects disclosed here to a wavelength-sweeping optical coherent tomography diagnosis apparatus.

1. Measurement Principle of Wavelength-Sweeping Optical Coherent Tomography Diagnosis Apparatus The principle of the wavelength-sweeping optical coherent tomography diagnosis apparatus is basically the same as the measurement principle of the optical coherent tomography diagnosis apparatus explained in connection with FIG. 1 and FIG. 2 in the aspect utilizing the optical coherence. Consequently, the description here will center primarily on differences of the apparatus here relative to the previously described optical coherent tomography diagnosis apparatus.

One different point for the measurement principle with respect to the optical coherent tomography diagnosis apparatus lies in the light source and, first, the coherent length thereof is different. In other words, while the light source of the optical coherent tomography diagnosis apparatus uses a low coherent light having the coherent length of around 10 μm to 20 μm, the light source of the wavelength-sweeping optical coherent tomography diagnosis apparatus uses a light having the coherent length of around 4 to 10 mm.

This is because, in case of the wavelength-sweeping optical coherent tomography diagnosis apparatus, the inspection range in the depth direction of the biological tissue depends on the coherent length while, in case of the optical coherent tomography diagnosis apparatus, the inspection range in the depth direction of the biological tissue depends on the movable range of the reference mirror. Then, in the wavelength-sweeping optical coherent tomography diagnosis apparatus, a light source having a comparatively long coherent length is used in order to fully cover the whole range in the depth direction of the biological tissue such as a blood vessel and the like.

A second difference involving the light source lies in an aspect that a light having different wavelengths are illuminated continuously in case of the wavelength-sweeping optical coherent tomography diagnosis apparatus.

In case of the optical coherent tomography diagnosis apparatus according to the first exemplified embodiment described mentioned above, the extraction of the reflection lights from respective points in the depth direction of the biological tissue is realized by the movement of the reference mirror and the resolution in the depth direction of the subject of measurement depended on the coherent length of the light illuminated.

On the contrary, in case of the wavelength-sweeping optical coherent tomography diagnosis apparatus, a light whose wavelength is changed continuously is illuminated and the intensity of the reflection light from the respective points in the depth direction of the biological tissue is changed depending on the difference of the frequency component of the coherent light.

Generally, when considering the frequency (inverse of wavelength) of the light to be swept as a time function shown in the following formula (Formula 1), it is possible to express the intensity of the coherent light as a time function shown in the following formula (Formula 2). In this case, $\Delta x$ denotes light path difference between the reference light and the subject light and $\Delta f$ denotes rate of frequency change in a unit time period (A, B, C indicate constant values).

$$f(t)=f_a+\Delta ft \quad \text{(Formula 1)}$$

$$l(t)=A+B\cos(C\Delta x(f_a+\Delta ft)) \quad \text{(Formula 2)}$$

As known from the formula 2, the frequency component of the time period change of the coherent light intensity l(t) is expressed by the light path difference $\Delta x$ and the frequency change $\Delta f$ of the wavelength-sweeping.

Consequently, knowing the frequency component of the coherent light, the coherent light intensity for every light path difference is known.

Thus, a time period required for obtaining a signal for one line becomes short and also, it is possible to make the image-creating depth deep.

Figure 15:
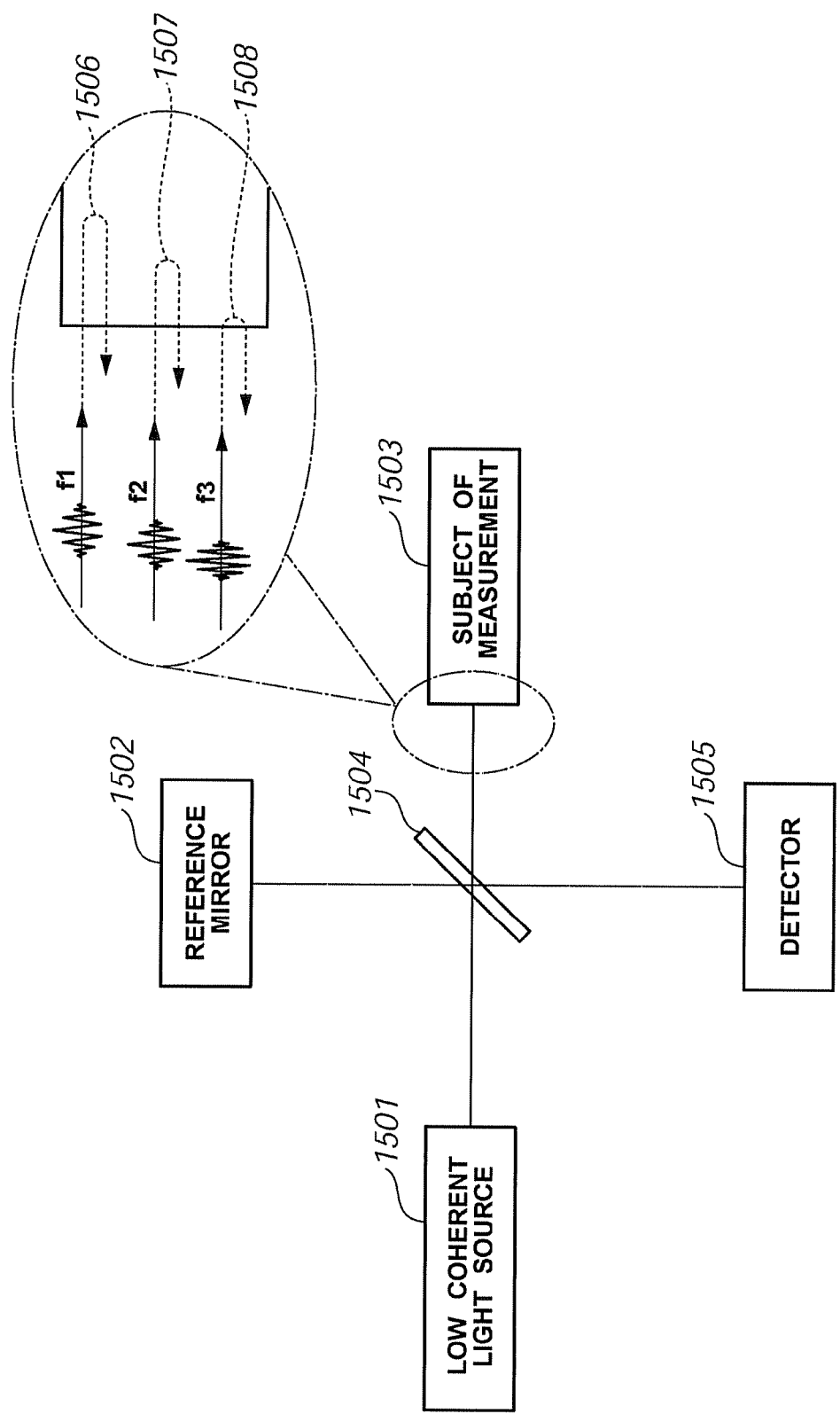
FIG. 15 is a schematic illustration of the basic principle of a wavelength-sweeping optical coherent tomography diagnosis apparatus disclosed here.

FIG. 15 is a general schematic illustration of the basic principle wavelength-sweeping optical coherent tomography diagnosis apparatus. In the same drawing, a wavelength-swept light source 1501 is a Swept Laser.

The lights including different frequencies, which are outputted sequentially from the wavelength-swept light source 1501, are split by a beam splitter 1504 and respective lights are directed to a reference mirror 1502 and a subject of measurement 1503. The reflection light returned from the subject of measurement 1503 side at that time includes reflection lights from various positions such as a reflection light reflected on the material body surface, a light reflected at a shallow position inside the material body, a light reflected at a deep portion inside the material body and the like.

As mentioned above, it is possible, in a detector 1505, to make structural information at a specified position in the depth direction of the subject of measurement visible by frequency-resolving the observed coherent light. As a result thereof, it is possible to form a tomographic image.

It should be noted that the light outputted from the wavelength-swept light source 1501 has a coherent length of around 4 to 10 mm and therefore, the whole inspection range in the depth direction of the subject of measurement can be fully covered, so that it happens that the reference mirror does not need to be operated and the reference mirror 1502 is to be arranged in a fixed manner at a fixed distance.

In this manner, it is not necessary to move the reference mirror mechanically, so that in case of a wavelength-sweeping optical coherent tomography diagnosis apparatus, the time period required for obtaining a signal for one line becomes short as compared with the optical coherent tomography diagnosis apparatus and it is possible to raise the frame rate thereof. While the maximum frame rate in the optical coherent tomography diagnosis apparatus is 15 fr/s, the frame rate of the wavelength-sweeping optical coherent tomography diagnosis apparatus is around 30 to 200 fr/s.

Primarily, in case of an optical coherent tomography diagnosis apparatus or a wavelength-sweeping optical coherent tomography diagnosis apparatus, the blood must be removed on an occasion of a diagnosis in order to avoid absorption of the light to a blood-cell component and in order to obtain a good image. For this reason, the time period in which the blood is removed must be made to be long if the frame rate is low and it is not preferable clinically. On the contrary, in case of a wavelength-sweeping optical coherent tomography diagnosis apparatus, it is possible to obtain an image of 30 mm or more in the axial direction of the blood vessel by the blood removal for a few seconds, so that there is a merit that the clinical problem can be lowered.

Figure 16:
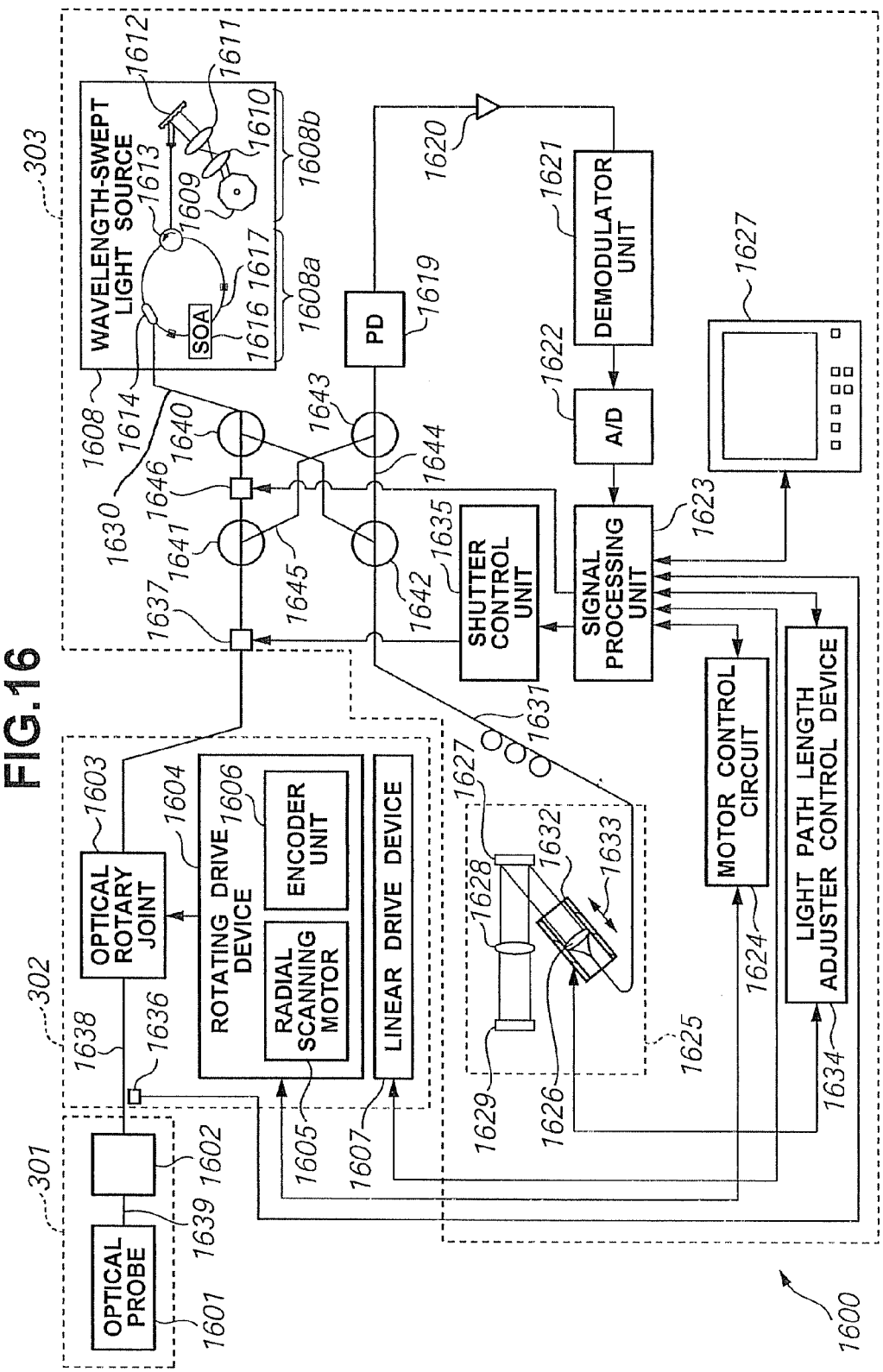
FIG. 16 is a schematic illustration of the wavelength-sweeping optical coherent tomography diagnosis apparatus shown in FIG. 15.

2. Features of Wavelength-Sweeping Optical Coherent Tomography Diagnosis Apparatus FIG. 16 is a schematic illustration of features of a wavelength-sweeping optical coherent tomography diagnosis apparatus 1600. The description which follows will primarily address differences with respect to the optical coherent tomography diagnosis apparatus which was explained above in connection with the first exemplified embodiment shown in FIG. 4.

1608 denotes a wavelength-swept light source, with a Swept Laser preferably being used. The Swept Laser 1608 is a kind of Extended-Cavity Laser composed of a SOA 1616 (semiconductor optical amplifier), an optical fiber 1617 coupled in a ring shape and a polygon scanning filter (1608b). The light outputted from the SOA 1616 proceeds to the optical fiber 1617 and enters into the polygon scanning filter 1608b, in which the light whose wavelength is selected is amplified in the SOA 1616 and finally outputted from the coupler 1614.

The polygon scanning filter 1608b selects the wavelength in combination of a diffractive grating 1612 for spectrally diffracting the light and a polygon mirror 1609. The light spectrally diffracted by the diffractive grating 1612 is focused on the surface of the polygon mirror 1609 by two pieces of lenses (1610, 1611). Thus, only the light of the wavelength which is perpendicular to the polygon mirror 1609 returns in the same light path and is outputted from the polygon scanning filter 1608b, so that time sweeping of the wavelength is carried out by rotating the mirror.

For the polygon mirror 1609, for example, a thirty-two polyhedral mirror is used and the rotational speed thereof is around 50000 rpm. According to a unique wavelength sweeping system formed by a combination of the polygon mirror 1609 and the diffractive grating 1612, it is possible to employ wavelength-sweeping of high-speed and of high-power output.

The light of the Swept Laser 1608 outputted from the coupler 1614 enters into one end of a first single-mode fiber 1630 and is transmitted to the distal surface side thereof. The first single-mode fiber 1630 is branched to a second single-mode fiber 1631 by an optical coupler unit 1640 on the way. The optical coupler unit refers to, for example, an optical component which can split one light signal into two or more outputs or can combine two or more inputted light signals into one output, and the light of the wavelength-swept light source 1608 is transmitted by being split into two outputs in the optical coupler unit 1640. The optical coupler 1640 here, and in other embodiments, constitutes an example of a branch portion (first branch portion) at which is branched the light transmitted from the source to the probe.

On the distal side of the first single-mode fiber 1630 from the optical coupler unit 1640, there are connected a frequency shifter 1646, an optical circulator 1641 and a shutter unit 1637.

Here, the shutter unit 1637 plays the role of controlling the emission of the light from the operation control unit 303 to the scanner/pullback unit 302 side. Also, the optical circulator 1641 is an optical component including three or more ports and plays the role of passing through the light which proceeds to the forward direction with low loss. Here and in the other disclosed embodiments, the optical circulator 1641 constitutes a second branch portion.

Also, the frequency shifter 1646 plays the role of shifting the frequency of the light transmitted to the distal surface side. Generally, the coherent signal strength obtained from the light having the same reflected intensity is strongest at a position at which the light path difference becomes 0 and is attenuating in accordance with the Gaussian function. Here, the light transmitted to the reference mirror through the second single-mode fiber 1631 is usually adjusted for the light path length such that the light path difference with respect to the light reflected from the probe surface becomes 0. In other words, it is adjusted such that the strength of the coherent signal with respect to the reflection light from the probe surface becomes the maximum and in a case in which the frequency shifter 1646 is not provided, it happens that the image area in the depth direction of the tomographic image obtained based on the coherent signal will become an image area centering around the probe surface. Here, in a case in which ±xmm centering around the probe surface is the image area, the image area in the minus direction (opposite direction with respect to the depth direction of the biological tissue) is an area not related to the biological tissue. Consequently, by shifting the frequency of the transmitted light using the frequency shifter 1646, for example, it becomes possible to set the image area in a plus direction (depth direction of the biological tissue) in which the biological tissue surface is made to be a start point and it becomes possible to enlarge the effective image area.

Referring to FIG. 16, the scanner/pullback unit 302 is provided with an optical rotary joint 1603 which couples a non-rotating portion and a rotating portion and transmits the light.

Further, at the distal tip of a third single-mode fiber 1638 in the optical rotary joint 1603, there is connected a connector portion 1602 of an optical probe 1601 detachably. Thus, the light from the wavelength-swept light source 1608 is transmitted into a fourth single-mode fiber 1639 which is inserted into the optical probe 1601 repeating the light transmission and reception and which is rotatingly drivable. Here, and in the other embodiments, the light path between the optical coupler unit 1640 and the optical probe 1601 constitutes a sample light path.

The attachment and the detachment of the connector portion 1602 of the optical probe are detected by a catheter connection detector unit 1636 and the detected result is inputted to a signal processing unit 1623. In the signal processing unit 1623, an open and close command for controlling the shutter unit 1637 is outputted with respect to a shutter control unit 1635 based on the inputted detected result, and in the shutter control unit 1635, the operation of the shutter unit 1637 is controlled based on the open and close command.

The light transmitted under a state in which the shutter unit 1637 is open is illuminated while being scanned radially from the distal side of the optical probe 1601 to the biological tissue side in the body cavity. Then, a portion of the reflection light diffused on the surface or in the inside of the biological tissue side is taken in by the optical probe 1601 and returns to the first single-mode fiber 1630 side via a reverse light path. Further, the light is shifted to a fifth single-mode fiber 1645 side by the optical circulator 1641.

It should be noted that the rotation unit side of the optical rotary joint 1603 is driven rotatingly by a radial scanning motor 1605 of a rotating drive device 1604. Also, the rotation angle of the radial scanning motor 1605 is detected by an encoder unit 1606. Further, the optical rotary joint 1603 includes a linear drive device 1607 and defines the operation in the insertion direction (axial direction) of the catheter unit 301 based on an instruction from the signal processing unit 1623. The axial direction movement is realized by a fact that the linear drive device 1607 operates based on a control signal from the signal processing unit 1623.

Here, it is possible for the radial scanning motor 1605 and the linear drive device 1607 to be connected detachably or to be constituted or formed integrally in one piece. Also, the movement in the axial direction by the linear drive device 1607 can be realized by way of a ball screw or the like.

Also, there is provided, on the distal side from the optical coupler unit 1640 of the second single-mode fiber 1631, with a variable mechanism 1625 of the light path length for fine-adjusting the light path length of the reference light.

The variable mechanism 1625 of this light path length includes a light-path length changer for changing a light path length corresponding to fluctuation of the lengths thereof so as to absorb the fluctuation of the lengths of individual optical probes in case of using optical probes exchangingly. Here and in the other disclosed embodiments, the light path between the optical coupler 1640 and the variable mechanism 1625 constitutes a reference light path.

The second single-mode fiber 1631 and a collimating lens 1626 are provided on one axis stage 1632 which is freely movable in the light axial direction thereof as shown by an arrow 1633, and a light-path length changer is formed.

Specifically, in case of exchanging the optical probe 1601, the one axis stage 1632 forms a light-path length changer having a variable range of the light path length such that the fluctuation of the light path length of the optical probe can be absorbed. Further, the one axis stage 1632 is provided also with a function as an adjuster for adjusting offset. For example, even in a case in which the distal tip of the optical probe 1601 is not closely-attached on the surface of the biological tissue, it becomes possible, by changing the light path length minutely depending on the one axis stage, to set a state of exerting interference from the surface position of the biological tissue.

The light which was fine-adjusted for the light path length by the variable mechanism 1625 of the light path length is shifted to a sixth single-mode fiber 1644 side by an optical circulator 1642 provided on the way of the second single-mode fiber 1631, is mixed with the light obtained from the fifth single-mode fiber 1645 side in an optical coupler unit 1643 and is light-received as a coherent light in a photo detector (for example, photodiode 1619).

The coherent light received by the photodiode 1619 is converted photoelectrically, is amplified by an amplifier 1620 and thereafter, is inputted to a demodulator unit 1621. In this demodulator unit 1621, there is performed a demodulation process for extracting only a signal component of the coherent light and the output thereof is inputted to an A/D converter 1622.

In the A/D converter 1622, digital data of one line (coherent light data) are generated by sampling the coherent light signal with 180 MHz for 2048 points. Here, a fact that the sampling frequency was selected to be 180 MHz is caused by an assumption that around 90% of the period (12.5 μsec) of the wavelength-sweeping is extracted as digital data of 2048 points in case of assuming that the repetition frequency of the wavelength-sweeping is 40 kHz and the present invention is not limited by this fact particularly.

The coherent light data of line unit which are generated in the A/D converter 1622 are inputted to the signal processing unit 1623. In this signal processing unit 1623, data in the depth direction are generated by frequency-resolving the coherent light data using FFT (Fast Fourie Transform) and by coordinate-converting this, tomographic images at respective positions in the blood vessel are formed and outputted by a predetermined frame rate to an LCD monitor 1627.

The signal processing unit 1623 is connected with a light path length adjuster control device 1634. The signal processing unit 1623 carries out position control of the one axis stage 1632 through the light path length adjuster control device 1634. Also, the signal processing unit 1623 is connected with a motor control circuit 1624 and stores the tomographic image in an inner memory in synchronism with the video synchronous signal when forming the tomographic image.

Also, the video synchronous signal of this motor control circuit 1624 is also transmitted to the rotating drive device 1604 and the rotating drive device 1604 outputs a drive signal in synchronism with the video synchronous signal.

3. Features of Catheter Connection Detector Unit

Figure 17:
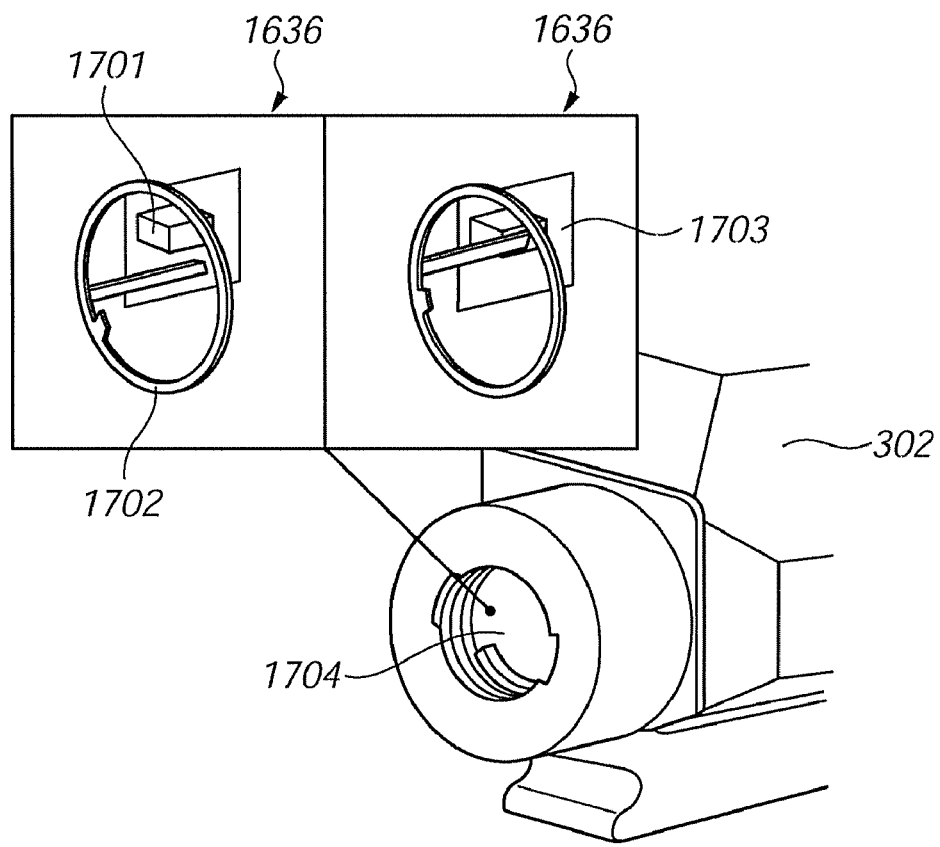
FIG. 17 is a views of a catheter connection detector unit. used in the apparatus shown in FIG. 16.

The construction of the catheter connection detector unit 1636 is described below with reference to FIGS. 17A-17C. FIG. 17A shows a distal side of the scanner/pullback unit 302 mounted with the catheter connection detector unit 1636. The catheter connection detector unit 1636 is mounted in an opening portion 1704 on the distal side of the scanner/pullback unit 302.

In the wavelength-sweeping optical coherent tomography diagnosis apparatus according to the present exemplified embodiment, a photo interrupter is to be used for the catheter connection detector unit 1636. As shown in FIG. 17B, there is provided a ring 1702 at the opening portion 1704 on the distal side and when the catheter unit 301 is connected to the scanner/pullback unit 302, the ring 1702 will rotate and this is detected by a photo interrupter 1701. FIG. 17C shows a state in which the photo interrupter 1701 detected the connection of the catheter unit 301 based on a fact that the ring 1702 rotates.

4. Construction of Shutter Unit and Shutter Control Unit

Figure 18:
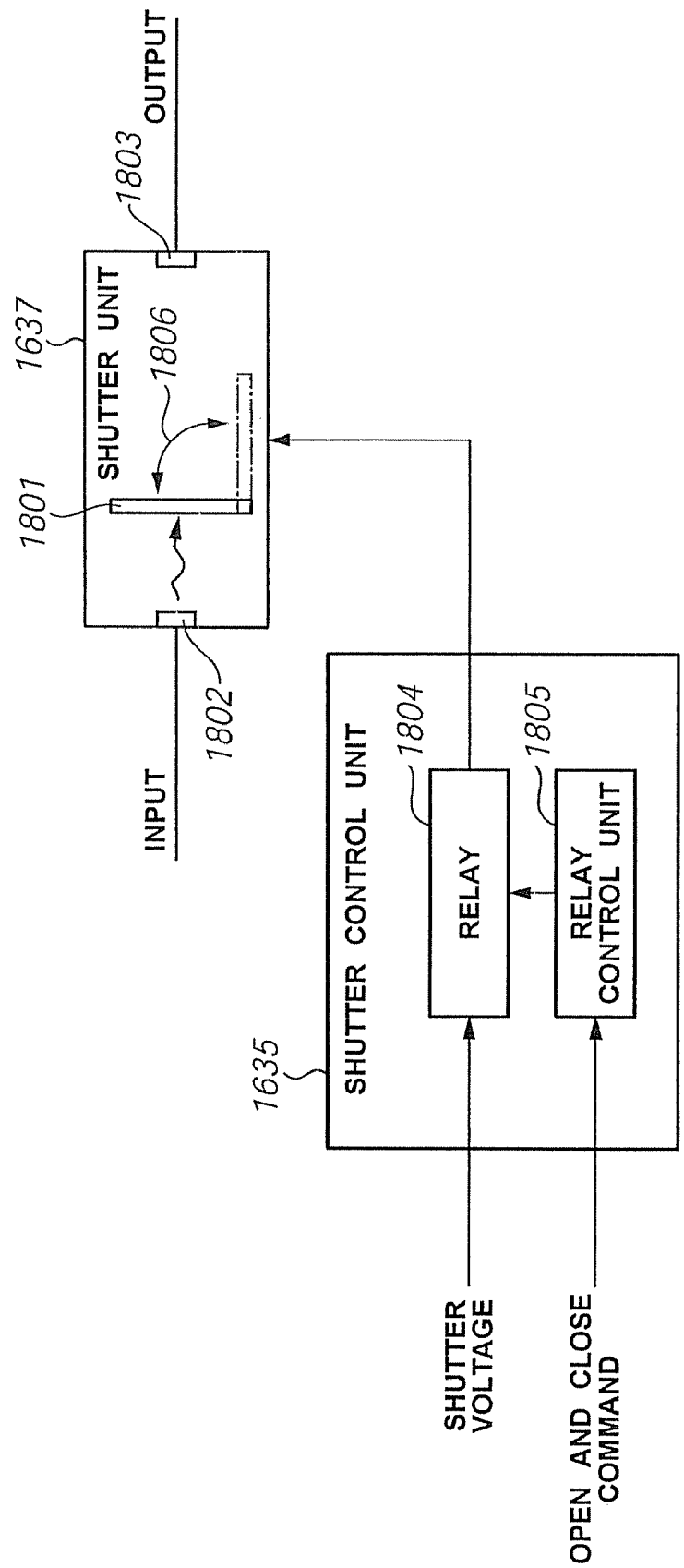
FIG. 18 is a schematic illustration of a shutter unit and a shutter control unit.

Next will be described the features of the shutter unit 1637 and the shutter control unit 1635. FIG. 18 schematically illustrates the shutter unit 1637 and the shutter control unit 1635.

The shutter control unit 1635 includes a relay control unit 1805 and a relay 1804. The relay control unit 1805 operates the relay 1804 depending on an open-command/close-command outputted from the signal processing unit 1623 based on a detected result of the catheter connection detector unit 1636. The relay 1804 is applied with a predetermined voltage from a power supply and the relay 1804 is opened and closed under the control of the relay control unit 1805.

On the other hand, the shutter unit 1637 includes a light incident port 1802 which the light of the wavelength-swept light source 1608 enters, a light emission port 1803 for transmitting the incident light from the light incident port 1802 with respect to the optical probe 1601, and a shielding body 1801 for shielding the light path on the light path between the light incident port 1802 and the light emission port 1803.

The shielding body 1801 operates freely rotatably in the direction of the arrow 1806 between a closed position (shielding position) for shielding the light path on the light path between the light incident port 1802 and the light emission port 1803 and an open position for not shielding the light path. The rotating movement between the closed position and the open position (non-shielding position) according to the shielding body 1801 is executed by the open and close operation of the relay 1804.

It should be noted, in a case in which the shielding body 1801 is in a close position, that the incident light from the light incident port 1802 is shielded by the shielding body 1801 and therefore, it never happens that light-emission is performed from the light emission port 1803.

5. Shutter Opening and Closing Process

Next, based on a detected result in the catheter connection detector unit 1636, it will be explained, by using FIG. 19, with respect to a flow of a shutter opening and closing process of the signal processing unit 1623 which outputs an open and close command with respect to the shutter control unit 1635.

Figure 19:
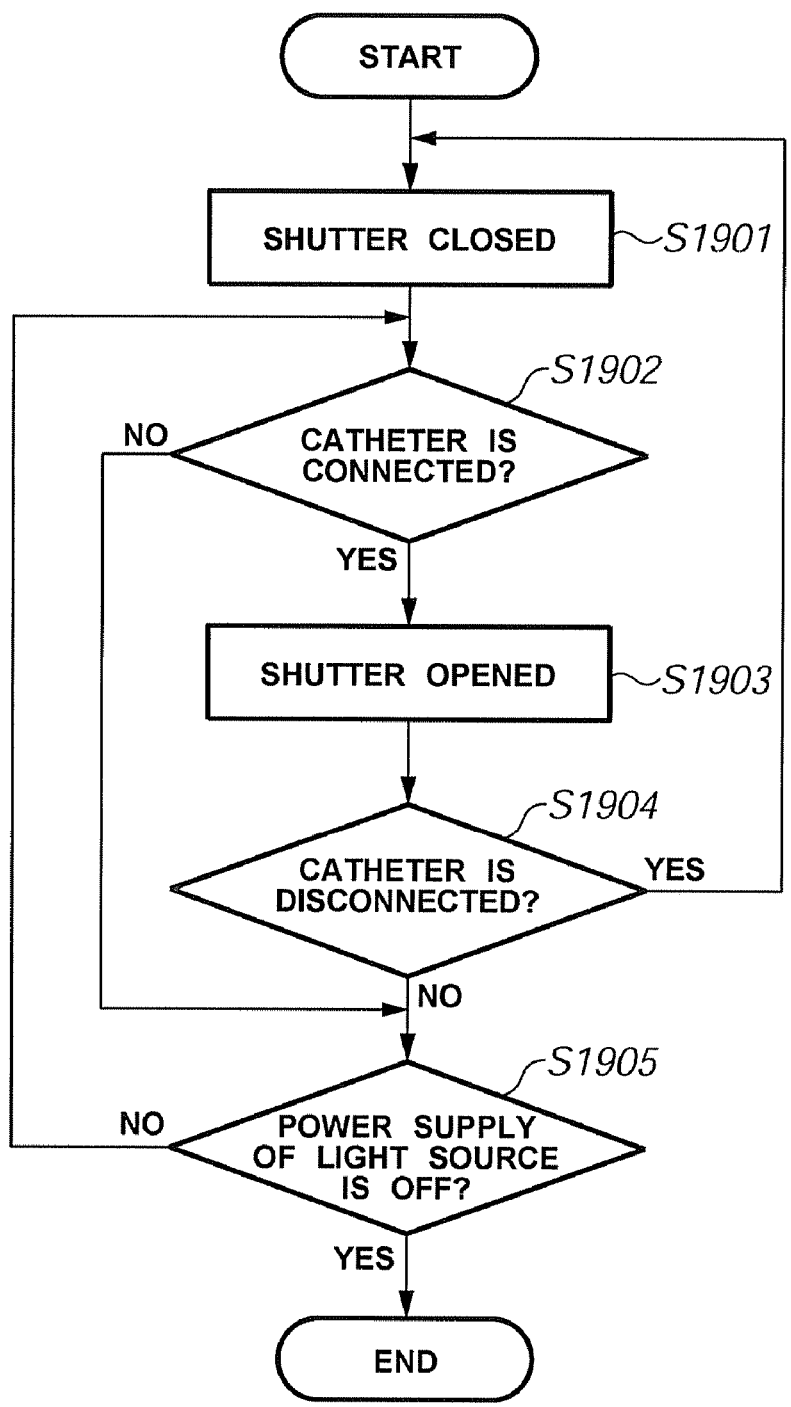
FIG. 19 is a flowchart showing operational aspects of a shutter opening and closing process of a wavelength-sweeping optical coherent tomography diagnosis apparatus according to an eighth exemplified embodiment disclosed here.

When the wavelength-swept light source 1608 starts driving (operating), a shutter opening and closing process starts as shown in FIG. 19. In step S1901, the shielding body 1801 is rotated to the close position by outputting a close command with respect to the shutter control unit 1635. Thus, it never happens that the light is emitted from the operation control unit 303 even in a case in which the wavelength-swept light source 1608 is driven.

In step S1902, it is judged whether or not the catheter unit 301 is connected based on a detected result from the catheter connection detector unit 1636. In a case in which it is judged in step S1902 that the catheter unit 301 is not connected, the flow proceeds to step S1905 and it is confirmed whether or not the wavelength-swept light source 1608 is in a non-drive state, and in a case in which it is in a non-drive state, the process ends. On the other hand, in a case in which the wavelength-swept light source 1608 is driven, the flow returns to step S1902 and the connection of the catheter unit 301 is observed.

In step S1902, in a case in which it is judged that the catheter unit 301 is connected, the flow proceeds to step S1903 and the shielding body 1801 is rotated to an open position by outputting an open command with respect to the shutter control unit 1635. Thus, the measuring light is emitted from the catheter unit 301. In other words, when the diagnosis preparation is completed in which the catheter unit 301 is connected to the scanner/pullback unit 302, a state arises in which the measuring light is emitted.

In step S1904, it is judged whether or not the catheter unit 301 becomes disconnected. In a case in which it is judged that the catheter unit 301 does not become disconnected, the flow proceeds to step S1905 and it is confirmed whether or not the wavelength-swept light source 1608 does not become a non-drive state. If it is determined that the wavelength-swept light source 1608 is driven, the flow returns to step S1902.

On the other hand, in a case in which it is judged that a disconnection state of the catheter unit 301 arises (the catheter becomes disconnected), the flow returns to step S1901 and the shielding body 1801 is rotated to the closed position by outputting a close command with respect to (from) the shutter control unit 1635.

In this manner, a shutter opening and closing process is executed in the signal processing unit 1623 during a period when the wavelength-swept light source 1608 is driven, and the measuring light is emitted only during a period when the catheter unit 301 is connected, and when the catheter unit 301 becomes disconnected, the shutter is closed so as not to emit the measuring light.

In the wavelength-sweeping optical coherent tomography diagnosis apparatus of this exemplified embodiment, the measuring light will never be emitted to the outside in a case in which the catheter unit is not connected, even in a case in which the wavelength-swept light source is driven, and it becomes possible to avoid reception of the measuring light before and after the diagnosis. In particular, with respect to the wavelength-swept light source, there is required a time period for the stabilization of the rotation speed of the polygon mirror which rotates high-speedily, so that a fact that the light source is not stopped has a beneficial result.

Ninth Exemplified Embodiment

The eighth exemplified embodiment described above employs a construction in which the measuring light is shielded by rotating the shutter to a closed position, that is by moving the shielding body onto the light path of the measuring light. However, the apparatus intended to be protected here is not limited in this regard and it is also possible to employ an arrangement that does not permit the light-emission of the measuring light, for example by deviating the light path of the measuring light to the direction of the shielding body.

Figure 20:
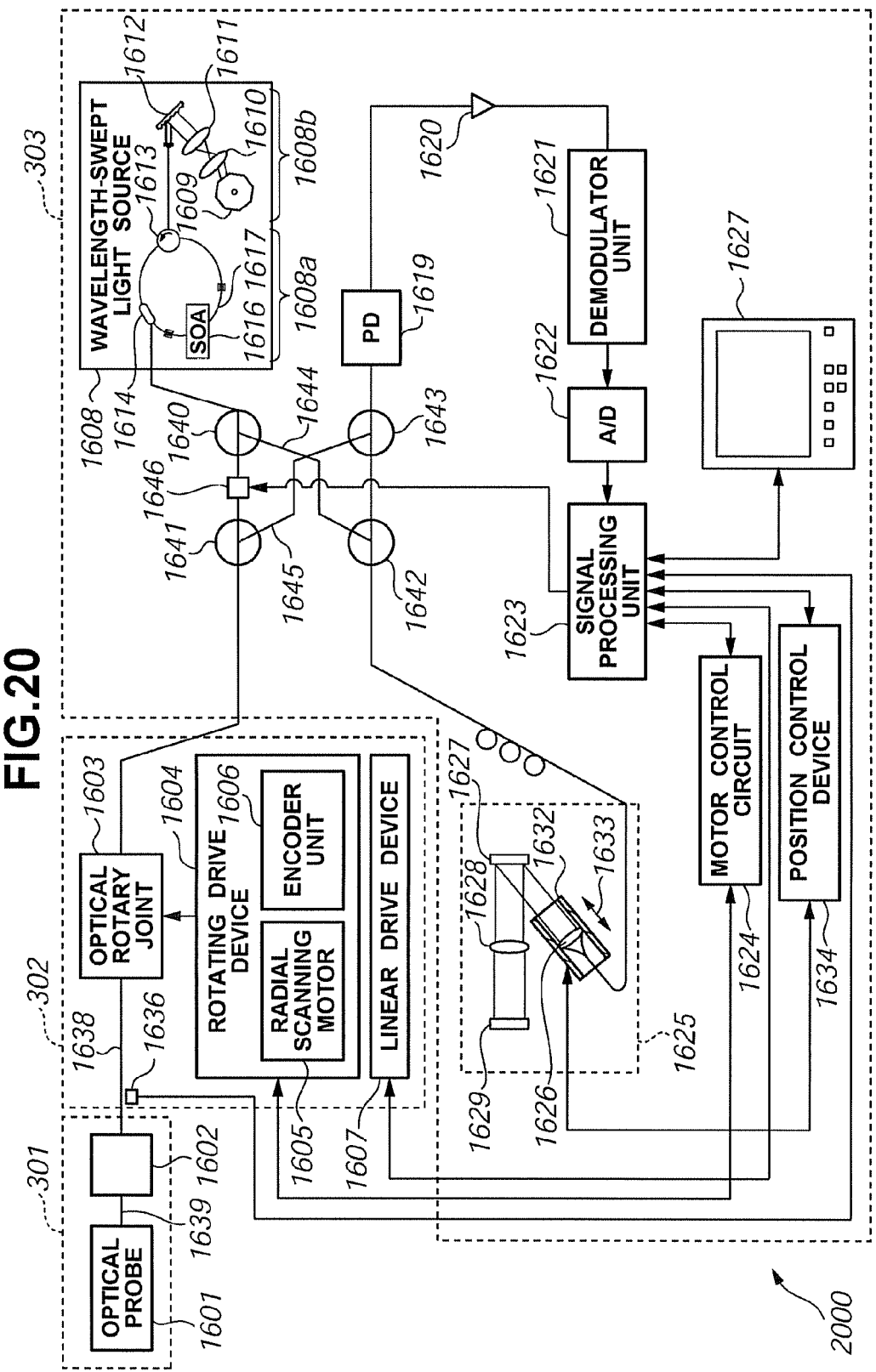
FIG. 20 is a schematic illustration of an optical coherent tomography diagnosis apparatus according to a ninth exemplified embodiment disclosed here.

1. Features of Wavelength-Sweeping Optical Coherent Tomography Diagnosis Apparatus FIG. 20 is a diagram showing features of a wavelength-sweeping optical coherent tomography diagnosis apparatus 2000 according to a ninth exemplified embodiment. The primary point of difference of this embodiment with respect to the construction of the wavelength-sweeping optical coherent tomography diagnosis apparatus 1600 according to the eighth exemplified embodiment described above in connection with FIG. 16 is that it does not include the shutter unit 1637 and the shutter control unit 1635, but rather operates the frequency shifter unit 1646 as a shutter unit instead of the shutter unit 1637.

2. Features of Frequency Shifter Unit

Figure 21:
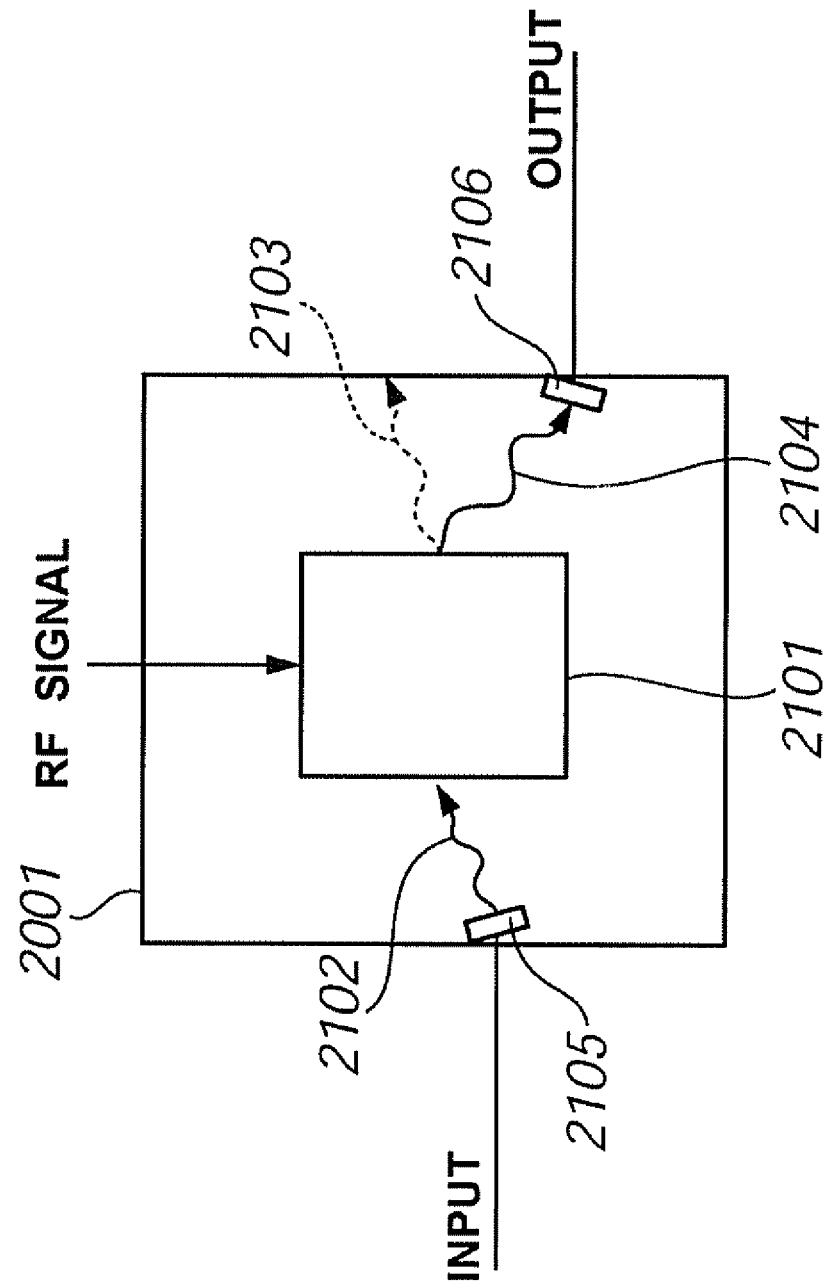
FIG. 21 is a view of a frequency shifter unit.

The construction of the frequency shifter unit 2001 is explained below with reference to FIG. 21. As shown in FIG. 21, the frequency shifter unit 2001 includes a light incident port 2105 which the light of the wavelength-swept light source 1608 enters, an acoustooptical device 2101 for shifting the light frequency by diffracting an incident light 2102 from the light incident port 2105, and a light emission port 2106 for emitting a light 2104 whose frequency is shifted.

In the frequency shifter unit 2001, when an RF signal is inputted from the signal processing unit 1623, the incident light 2102 entering the light incident port 2105 is diffracted in the acoustooptical device 2101 and light-emission is carried out from the light emission port 2106. On the contrary, in a case in which the RF signal is not inputted from the signal processing unit 1623, diffraction of the light does not occur in the acoustooptical device 2101, so that the incident light 2102 from the light incident port 2105 does not go toward the direction of the light emission port 2106 and is reflected in the housing constituting the frequency shifter unit 2001 (see 2103). Therefore, it never happens that the light-emission is carried out from the light emission port 2106.

In this manner, the light path between the light incident port 2105 and the light emission port 2106 is controlled in the frequency shifter unit 2001 depending on the presence or absence of the RF signal and in a case in which it is not desired for the light to be emitted from the light emission port 2106, the housing of the frequency shifter unit 2001 functions as a shielding body.

3. Control Process of Frequency Shifter Unit

Figure 22:
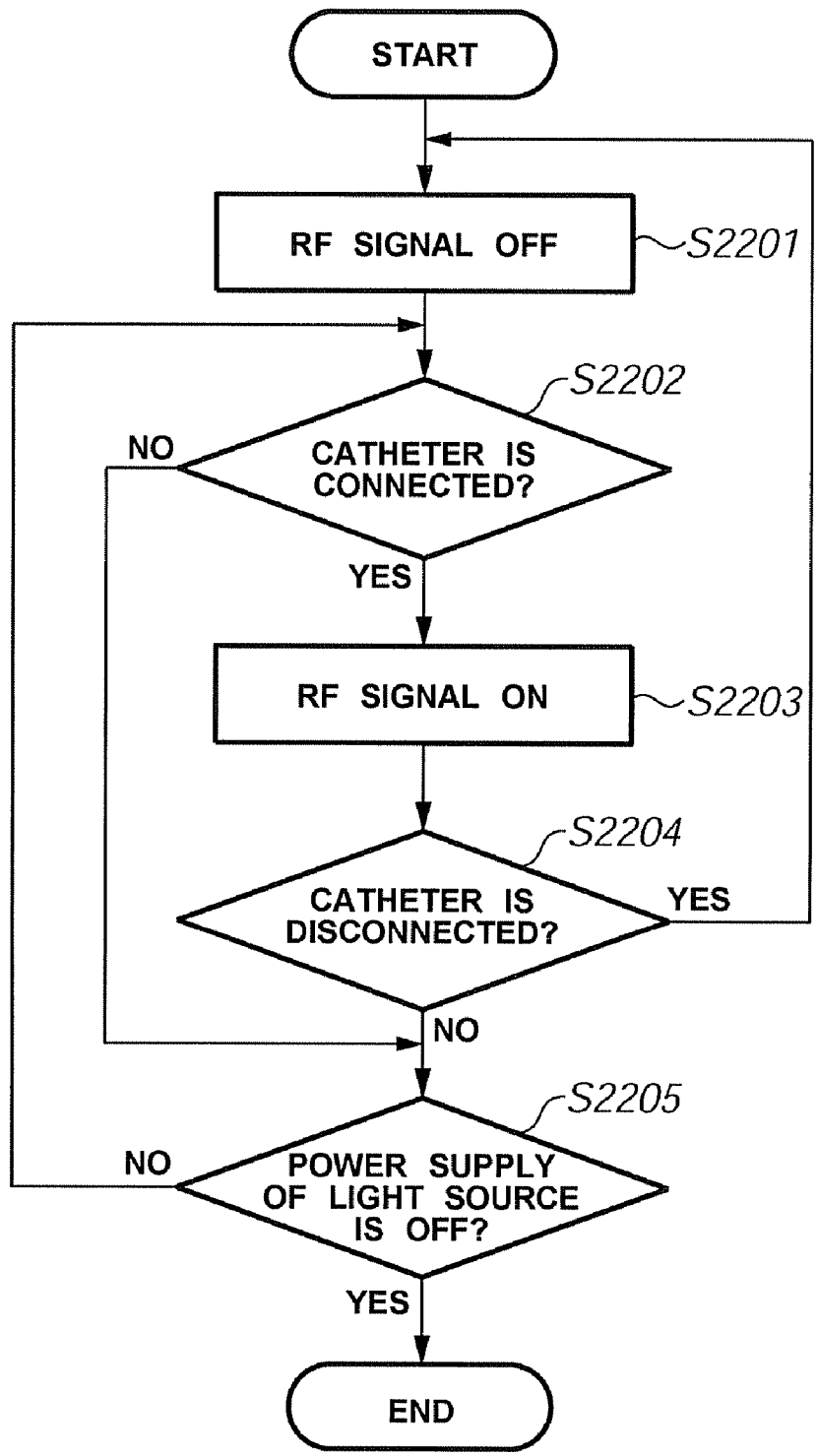
FIG. 22 is a flowchart showing operational aspects of a control process of the frequency shifter unit of the wavelength-sweeping optical coherent tomography diagnosis apparatus according to the ninth exemplified embodiment.

Based on a detected result in the catheter connection detector unit 1636, FIG. 22 illustrates a control process of the signal processing unit 1623 which controls the RF signal outputted with respect to the frequency shifter unit 2001. When the wavelength-swept light source 1608 starts the drive, a control process shown in FIG. 22 starts. In step S2201, the RF signal outputted with respect to the frequency shifter unit 2001 is turned OFF. Thus, even in a case in which the wavelength-swept light source 1608 starts the drive, it never happens that the light will be emitted from the operation control unit 303.

In step S2202, it is judged whether or not the catheter unit 301 is connected based on a detected result from the catheter connection detector unit 1636. In a case in which it is judged in step S2202 that the catheter unit 301 is not connected, the flow proceeds to step S2205 and it is confirmed whether or not the wavelength-swept light source 1608 is in a non-drive state, and in a case in which it is in a non-drive state, the process is ended. On the other hand, in a case in which the wavelength swept source 1608 is driven, the flow returns to step S2202 and the connection of the catheter unit 301 is confirmed.

In step S2202, in a case in which it is judged that the catheter unit 301 is connected, the flow proceeds to step S2203 and the incident light from the light incident port 2105 is diffracted, and the light is emitted from the light emission port 2106 by outputting an RF signal with respect to the frequency shifter unit 2001. Thus, the measuring light is emitted from the catheter unit 301. In other words, when the diagnosis preparation is completed in which the catheter unit 301 is connected to the scanner/pullback unit 302, a state is achieved in which the measuring light is emitted.

In step S2204, it is judged whether or not the catheter unit 301 becomes in a disconnection state. In a case in which it is judged that the catheter unit 301 is not in a disconnection state, the flow proceeds to step S2205 and it is observed whether or not the wavelength-swept light source 1608 is in a non-drive state. Here, in a case in which the wavelength-swept light source 1608 is driven, the flow returns to step S2202.

On the other hand, in a case in which it is judged that the catheter unit 301 is in a disconnection state, the flow returns to step S2201 and the RF signal outputted from the frequency shifter unit 2001 is turned OFF.

In this manner, a control process of the frequency shifter unit 2001 is executed in the signal processing unit 1623 during a period when the wavelength-swept light source 1608 is driven and the measuring light is emitted only during a period when the catheter unit 301 is connected, and when the catheter unit 301 becomes disconnected, the frequency shifter unit 2001 is controlled so as not to emit the measuring light.

The wavelength-sweeping optical coherent tomography diagnosis apparatus according to the present exemplified embodiment is such that the measuring light will never be emitted to the outside in a case in which the catheter unit is not connected, even in a case in which the wavelength swept source is driven, and it becomes possible to avoid reception of the measuring light before and after the diagnosis.

Here, in this embodiment, the frequency shifter unit for adjusting the emitted measuring light is commonly used to move the emission of the measuring light, so that there is obtained a collateral effect that the apparatus cost can be reduced as compared with a case as the exemplified embodiment mentioned above in which a shutter unit and a shutter control unit are provided separately.

Tenth Exemplified Embodiment

The eighth and ninth exemplified embodiments described above employ a construction in which the measuring light is emitted during a period when the catheter unit is connected, but the apparatus here is not limited in this regard. Since the optical probe does not rotate during the time from when the catheter unit is connected to the time when the measurement starts after the catheter unit is inserted into blood vessel, it happens that the emitted measuring light keeps on illuminating a specified direction. As a result thereof, it is possible that some sort of influence may also be exerted on the biological tissue.

Consequently, in the present exemplified embodiment, there is employed an arrangement in which the open and close of the shutter unit is controlled under a condition in which it is connected with the catheter unit and also the optical probe is rotated. Hereinafter, details will be explained with respect to the wavelength-sweeping optical coherent tomography diagnosis apparatus according to the present exemplified embodiment.

1. Features of Wavelength-Sweeping Optical Coherent Tomography Diagnosis Apparatus The features of the wavelength-sweeping optical coherent tomography diagnosis apparatus according to the present exemplified embodiment is basically the same as that of FIG. 16 and so a detailed explanation will not be repeated. The apparatus is constructed such that the presence or absence of the rotation of the optical probe 1601 is judged by the signal processing unit 1623 which received the output of the encoder unit 1606 through the motor control circuit 1624.

2. Shutter Opening and Closing Process

Figure 23:
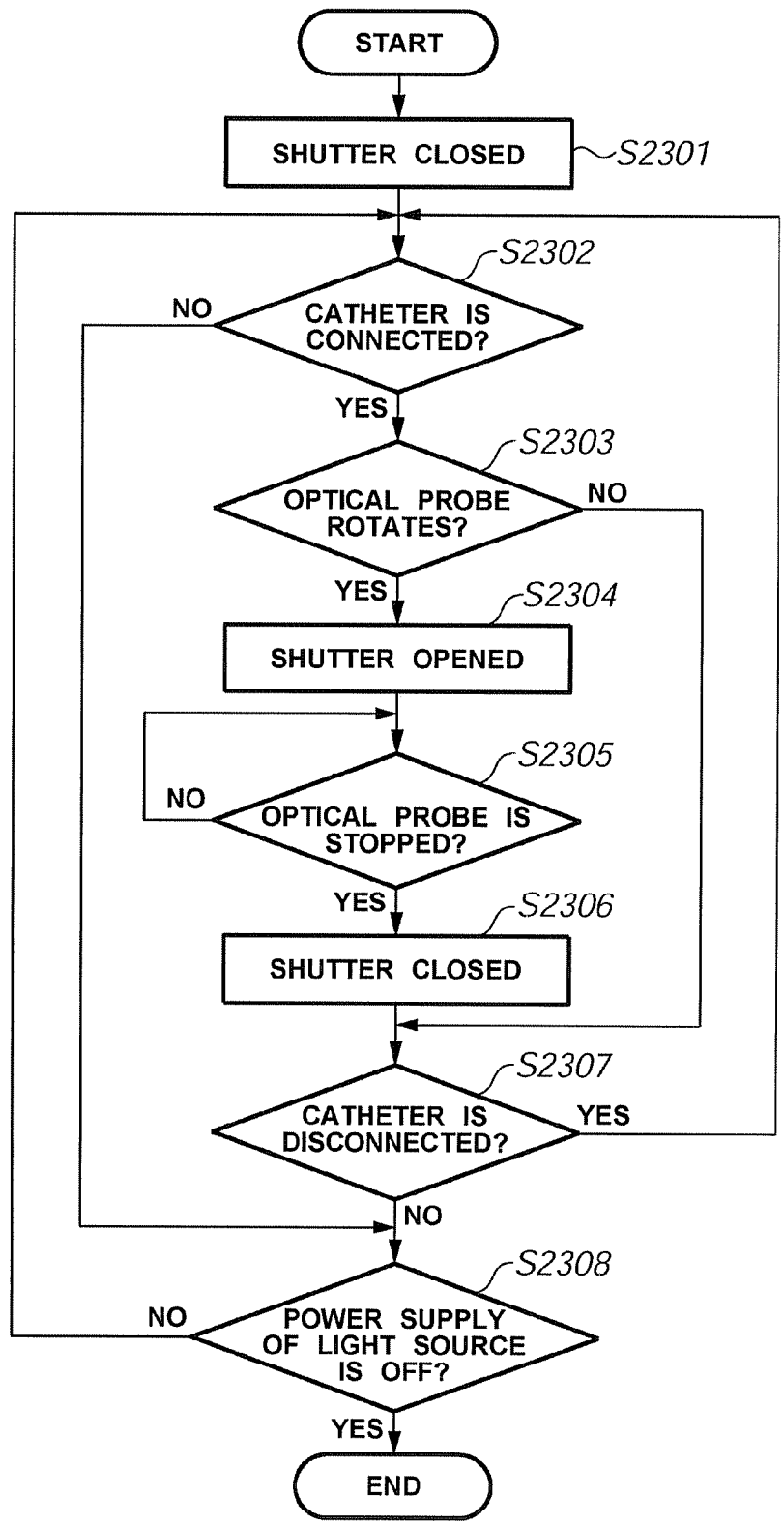
FIG. 23 is a flowchart showing operational aspects of a shutter control process of a wavelength-sweeping optical coherent tomography diagnosis apparatus according to a tenth exemplified embodiment disclosed here.

FIG. 23 illustrates the shutter opening and closing process in the wavelength-sweeping optical coherent tomography diagnosis apparatus according to the present exemplified embodiment.

When the wavelength swept source 1608 starts the drive (operates), a shutter opening and closing process starts as shown in FIG. 23. In step S2301, the shielding body 1801 is rotated to the close position by outputting a close command with respect to the shutter control unit 1635. Thus, it never happens that the light is emitted from the operation control unit 303 even in a case in which the wavelength-swept light source 1608 starts the drive.

In step S2302, it is judged whether or not the catheter unit 301 is connected based on a detected result from the catheter connection detector unit 1636. In a case in which it is judged in step S2302 that the catheter unit 301 is not connected, the flow proceeds to step S2308 and it is confirmed whether or not the wavelength-swept light source 1608 is in a non-drive state, and in a case in which it is in a non-drive state, the process is ended. On the other hand, in a case in which the wavelength-swept light source 1608 is driven, the flow returns to step S2302 and the connection of the catheter unit 301 is observed.

In a case in which it is judged in step S2302 that the catheter unit 301 is connected, the flow proceeds to step S2303 and it is judged based on the output of the encoder unit 1606 whether or not the optical probe 1601 rotates. In step S2303, in a case in which it is judged that the optical probe 1601 does not rotate, the flow proceeds to step S2307 and it is judged whether or not the catheter unit 301 becomes in a disconnection state. In a case in which it is judged that the catheter unit 301 is not in a disconnection state, the flow proceeds to step S2308 and drive/non-drive of the wavelength-swept light source 1608 is confirmed. If the result at step S2308 is NO, the flow returns to step S2302.

On the other hand, in a case in which it is judged in step S2303 that the optical probe 1601 rotates, the flow proceeds to step S2304 and the shielding body 1801 is rotated to the open position by outputting an open command with respect to the shutter control unit 1635. Thus, the measuring light is emitted from the catheter unit 301. In other words, it becomes in a state in which the catheter unit 301 is connected to the scanner/pullback unit 302 and the measuring light is to be emitted when the rotation of the optical probe is started.

In step S2305, it is judged whether or not the rotation of the optical probe 1601 is stopped based on the output of the encoder unit 1606. In step S2305, in a case in which it is judged that the optical probe 1601 does not rotate, the flow proceeds to step S2306 and the shielding body 1801 is rotated to the close position by outputting a close command with respect to the shutter control unit 1635.

In step S2307, it is judged whether or not the catheter unit 301 is in a disconnection state. In a case in which it is judged in step S2307 that the catheter unit 301 becomes in a disconnection state, the flow returns to step S2302 and it is observed whether or not the catheter unit 301 is connected.

On the other hand, in a case in which it is judged in step S2307 that the catheter unit 301 is not in a disconnected state, the drive/non-drive of the wavelength-swept light source 1608 is confirmed in step S2308 and thereafter, when a drive state is confirmed, the flow returns to step S2302.

In this manner, in the signal processing unit 1623, a shutter opening and closing process is executed during a period when the wavelength-swept light source 1608 is driven, and the measuring light is emitted only during a period when the catheter unit 301 is connected and also the optical probe rotates, and the shutter is closed to not emit the measuring light in a case in which the optical probe does not rotate although the catheter unit 301 is connected or in a case in which the catheter unit 301 is not connected.

In the wavelength-sweeping optical coherent tomography diagnosis apparatus relating to the present exemplified embodiment, the measuring light will never be emitted if it is not in a state in which the catheter unit is connected and also the optical probe rotates even in a case in which the wavelength-swept light source is driven, and it becomes possible to avoid reception of the measuring light before and after the diagnosis.

Eleventh Exemplified Embodiment

The tenth exemplified embodiment described above employs an arrangement in which the shutter is opened and the measuring light is emitted in a case in which the catheter unit is connected and the optical probe is in a rotating condition, but the present invention is not limited in this regard. It is possible, similar to the ninth exemplified embodiment discussed above, to employ a constitution in which the operation of the frequency shifter is to be controlled under the state thereof.

1. Features of Wavelength-Sweeping Optical Coherent Tomography Diagnosis Apparatus The features of the wavelength-sweeping optical coherent tomography diagnosis apparatus according to the present exemplified embodiment are basically the same as those associated with the apparatus illustrated in FIG. 16 and so an explanation of such features will not be repeated. Here, the presence or absence of the rotation of the optical probe 1601 is judged by the signal processing unit 1623 which receives the output of the encoder unit 1606 through the motor control circuit 1624.

2. Control Process of Frequency Shifter

Figure 24:
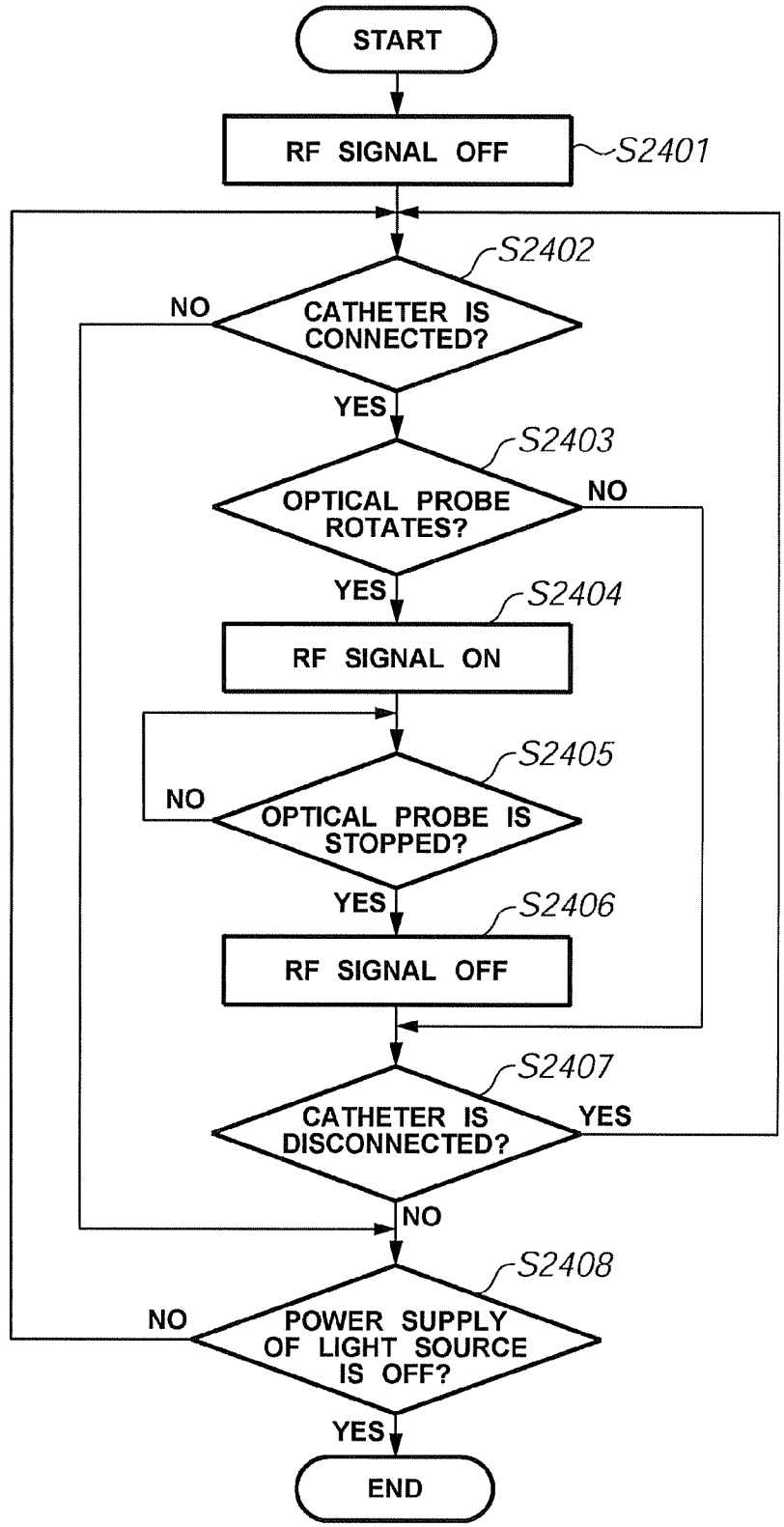
FIG. 24 is a flowchart showing operational aspects of a control process of the frequency shifter unit of the wavelength-sweeping optical coherent tomography diagnosis apparatus according to an eleventh exemplified embodiment disclosed here.

FIG. 24 illustrates the control process of the frequency shifter unit 2001 in the wavelength-sweeping optical coherent tomography diagnosis apparatus according to the present exemplified embodiment.

When the wavelength-swept light source 1608 starts driving (operation), a control process shown in FIG. 24 will start. In step S2401, the RF signal outputted with respect to the frequency shifter unit 2001 is turned OFF. Thus, even in a case in which the wavelength-swept light source 1608 starts the drive, it never happens that the light will be emitted from the operation control unit 303.

In step S2402, it is judged whether or not the catheter unit 301 is connected based on a detected result from the catheter connection detector unit 1636. In a case in which it is judged in step S2402 that the catheter unit 301 is not connected, the flow proceeds to step S2408 and it is confirmed whether or not the wavelength-swept light source 1608 is in a non-drive state, and in a case in which it is in a non-drive state, the process is ended. On the other hand, in a case in which the wavelength-swept light source 1608 is driven, the flow returns to step S2402 and the connection of the catheter unit 301 is observed.

In step S2402, in a case in which it is judged that the catheter unit 301 is connected, the flow proceeds to step S2403 and it is judged based on the output of the encoder unit 1606 whether or not the optical probe 1601 rotates. In step S2403, in a case in which it is judged that the optical probe 1601 is not rotating, the flow proceeds to step S2407 and it is judged whether or not the catheter unit 301 is in a disconnection state. In a case in which it is judged that the catheter unit 301 is not in a disconnection state, the flow proceeds to step S2408 where drive/non-drive of the wavelength-swept light source 1608 is confirmed, and thereafter when operation of the wavelength-swept light source 1608 is determined, the flow returns to step S2402.

On the other hand, in a case in which it is judged in step S2403 that the optical probe 1601 is rotating, the flow proceeds to step S2404 and the incident light from the light incident port 2105 is diffracted, and the light is emitted from the light emission port 2106 by outputting an RF signal with respect to the frequency shifter unit 2001. Thus, the measuring light is emitted from the catheter unit 301. In other words, a state is achieved in which the catheter unit 301 is connected to the scanner/pullback unit 302 and the measuring light is to be emitted when the rotation of the optical probe is started.

In step S2405, it is judged whether or not the rotation of the optical probe 1601 is stopped based on the output of the encoder unit 1606. In step S2405, in a case in which it is judged that the optical probe 1601 is not rotating, the flow proceeds to step S2406 and the RF signal outputted with respect to frequency shifter unit 2001 is turned OFF.

In step S2407, it is judged whether or not the catheter unit 301 is in a disconnection state. In a case in which it is judged in step S2407 that the catheter unit 301 is disconnected, the flow returns to step S2402 and it is observed whether or not the catheter unit 301 is connected.

On the other hand, in a case in which it is judged in step S2407 that the catheter unit 301 does not become in a disconnection state, the drive/non-drive of the wavelength-swept light source 1608 is confirmed in step S2408 and thereafter, the flow returns to step S2402.

In this manner, a control process of the frequency shifter unit 2001 is executed in the signal processing unit 1623 during a period when the wavelength-swept light source 1608 is driven and the measuring light is emitted only during a period when the catheter unit 301 is connected and also the optical probe rotates, and the frequency shifter unit 2001 is controlled so as not to emit the measuring light in a case in which the optical probe does not rotate although the catheter unit 301 is connected, or in a case in which the catheter unit 301 is not connected.

In the optical coherent tomography diagnosis apparatus relating to the present exemplified embodiment, the measuring light will never be emitted to the outside if it is not in a state in which the catheter unit is connected and also the optical probe rotates, even in a case in which the wavelength-swept light source is driven, and it is thus possible to avoid reception of the measuring light before and after the diagnosis.

Twelfth Exemplified Embodiment

In view of an aspect in the tenth and the eleventh exemplified embodiments discussed above that there is a possibility for the emitted measuring light to illuminate a specified region for a relatively long time period until the optical probe starts the rotation in a case in which the catheter is connected, there is employed a construction in which the measuring light is controlled such that it will be never emitted to the outside.

However, the apparatus to be protected here is not limited by this construction. For example, based on a fact that there is no significant influence on a human body if the illumination is for a short time period even if it is in a period when the catheter is connected and until the optical probe rotates, it is also possible to perform a shutter opening and closing process or a control process of the frequency shifter unit by limiting the time period for emitting the measuring light.

Figure 25:
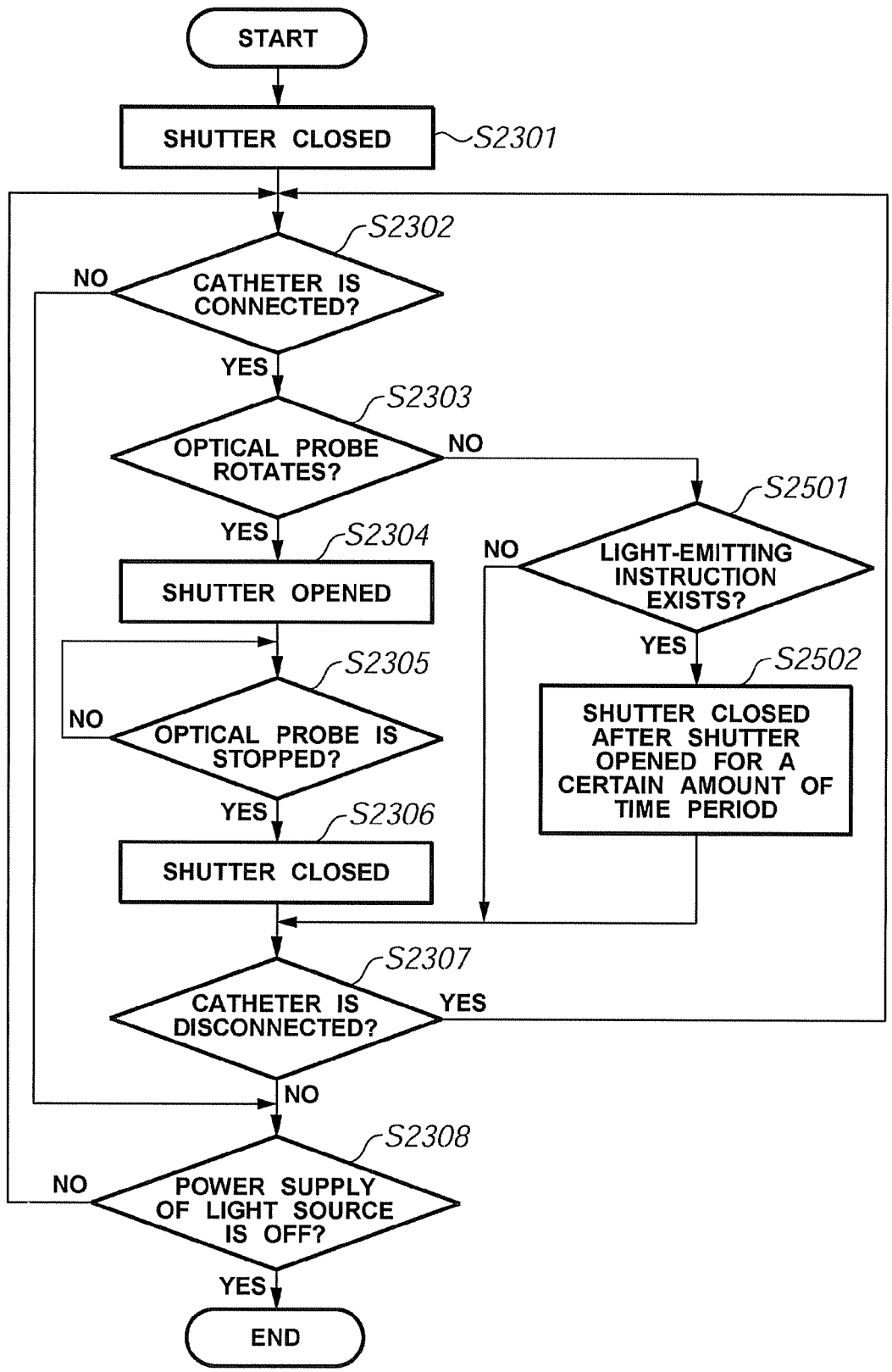
FIG. 25 is a flowchart showing operational aspects of a shutter control process of the wavelength-sweeping optical coherent tomography diagnosis apparatus according to a twelfth exemplified embodiment disclosed here.

FIG. 25 is a flowchart showing a shutter opening and closing process in the optical coherent tomography diagnosis apparatus according to the present exemplified embodiment.

Aspects of the shutter opening and closing process shown in FIG. 25 are similar to aspects of the process shown in FIG. 23, and so common reference numerals are used and a detailed description of such common aspects is not repeated. The description below focuses primarily on aspects of the shutter opening and closing process that differ from those described previously.

In a case in which it is judged in step S2303 that the optical probe 1601 does not rotate, the flow proceeds to step S2501. In step S2501, it is judged whether or not the signal processing unit 1623 accepted a light-emitting instruction. The light-emitting instruction in a state in which the optical probe 1601 is non-rotational means, for example, a case in which the operator inputs a light-emitting instruction manually and the signal processing unit 1623 recognizes this or the like.

In step S2501, in a case in which it is judged that there is no light-emitting instruction, the flow proceeds to step S2307. On the other hand, in a case in which it is judged in step S2501 that there is a light-emitting instruction, the flow proceeds to step S2502 and the shielding body 1801 is rotated to the open position by outputting an open command with respect to the shutter control unit 1635. Further, after a predetermined time period, the shielding body 1801 will be rotated to the close position by outputting a close command with respect to the shutter control unit 1635.

Thus, in a state in which the catheter unit 301 is connected, it becomes possible even in a case in which the optical probe 1601 does not rotate to emit the measuring light limited by a predetermined time period under an instruction of the operator.

In this present exemplified embodiment, a situation was explained in which the shutter unit 1637 is controlled, but it is possible to execute a similar process also with respect to a case in which the frequency shifter unit 2001 is to be controlled.

Thirteenth Exemplified Embodiment

The eighth and the ninth exemplified embodiments described above employ a construction in which the measuring light is controlled so as not to be emitted until the catheter is connected and the measuring light is controlled so as to be emitted after the catheter is connected, and the tenth and the eleventh exemplified embodiments mentioned above employ a construction in which the measuring light is further controlled so as not to be emitted until the optical probe rotates even if the catheter is connected and the measuring light is controlled so as to be emitted only when the optical probe is in a rotation state, but the present invention is not limited in these regards.

Generally, the measuring light emitted from the distal portion of the scanner and pull-back unit 302 in a state in which the catheter is disconnected will scatter, so that there are a lot of situations in which no problem occurs even if it is illuminated on a human body for a long time period. On the contrary, the light emitted from the distal tip of the optical probe by connecting the catheter is focused by a lens, so that there is a higher possibility that some sort of influence occurs in a case in which it is illuminated on a human body for a relatively long time period.

Consequently, the present exemplified embodiment employs a construction in which the measuring light is emitted until the catheter is connected and the measuring light is controlled so as not to be emitted during the period of time from when the catheter is connected to when the optical probe starts rotating. Hereinafter, it will be explained with respect to a flow of a shutter opening and closing process and also of a control process of the frequency shifter according to the present exemplified embodiment.

Figure 26:
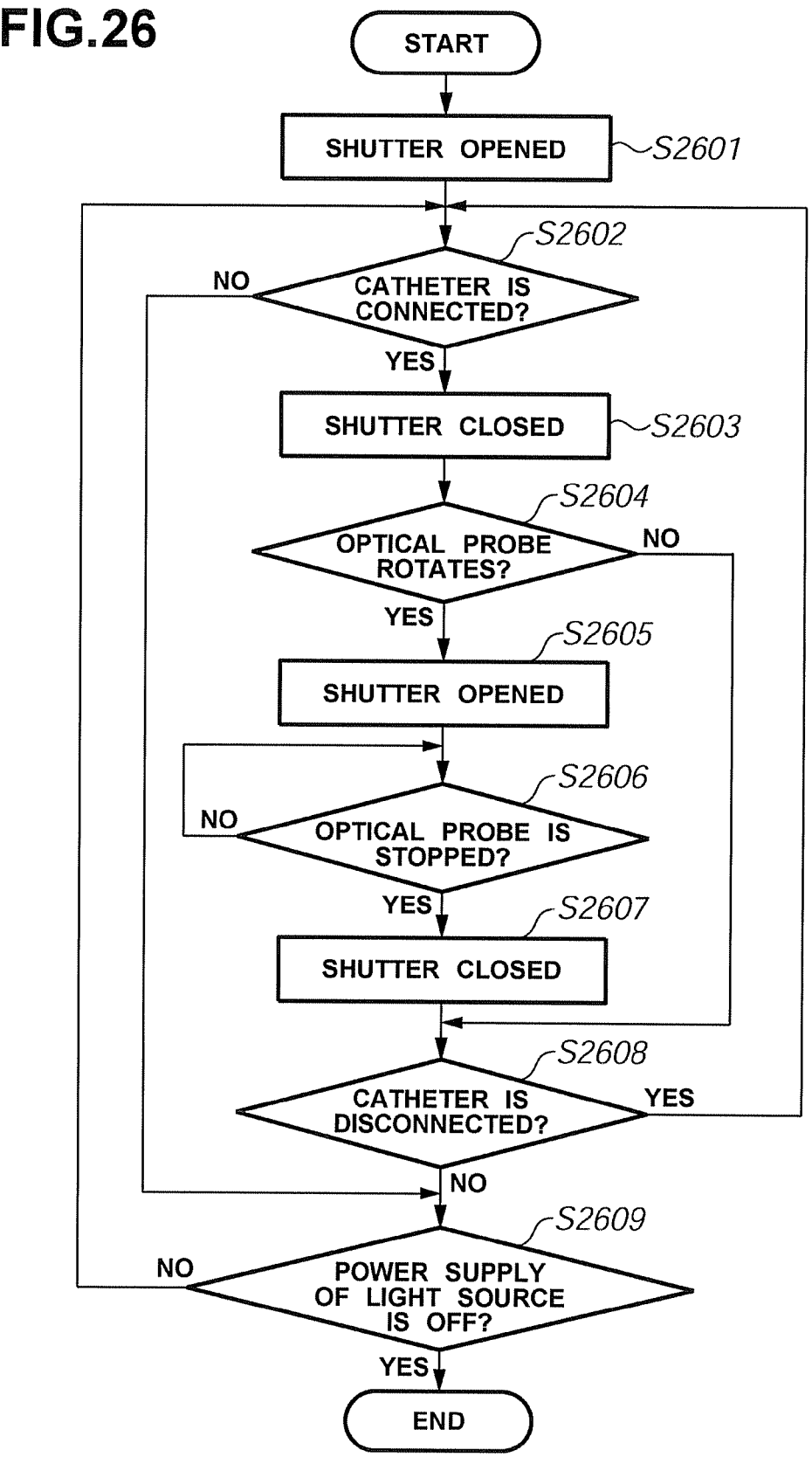
FIG. 26 is a flowchart showing operational aspects of a shutter control process of the wavelength-sweeping optical coherent tomography diagnosis apparatus according to a thirteenth exemplified embodiment disclosed here.

FIG. 26 is a flowchart showing a shutter opening and closing process in the optical coherent tomography diagnosis apparatus according to the present exemplified embodiment.

When the wavelength-swept light source 1608 starts driving (operating), a shutter opening and closing process shown in FIG. 26 starts. In step S2601, the shielding body 1801 is rotated to the open position by outputting an open command with respect to the shutter control unit 1635.

In step S2602, it is judged whether or not the catheter unit 301 is connected based on a detected result from the catheter connection detector unit 1636. When it is judged in step S2602 that the catheter unit 301 is not connected, the flow proceeds to step S2609 and it is confirmed whether or not the wavelength-swept light source 1608 is in a non-drive state, and in a case in which it is in a non-drive state, the process is ended. On the other hand, in a case in which the wavelength-swept light source 1608 is driven, the flow returns to step S2602 and the connection of the catheter unit 301 is observed.

In step S2602, when it is judged that the catheter unit 301 is connected, the flow proceeds to step S2603 and the shielding body 1801 is rotated to the close position by outputting a close command by the shutter control unit 1635. Thus, it never happens that the measuring light will be emitted after the catheter unit 301 is connected until the optical probe 1601 rotates.

In step S2604, based on the output of the encoder unit 1606, it is judged whether or not the optical probe 1601 rotates. In step S2604, in a case in which it is judged that the optical probe 1601 does not rotate, the flow proceeds to step S2608 and it is judged whether or not the catheter unit 301 is in a disconnection state. In a case in which it is judged that the catheter unit 301 is not in a disconnection state, the flow proceeds to step S2609 and drive/non-drive of the wavelength-swept light source 1608 is confirmed, and thereafter the flow returns to step S2602.

On the other hand, when it is judged in step S2604 that the optical probe 1601 rotates, the flow proceeds to step S2605 and the shielding body 1801 is rotated to the open position by outputting an open command with respect to the shutter control unit 1635. Thus, the measuring light is emitted from the catheter unit 301. In other words, a state results in which the catheter unit 301 is connected to the scanner/pullback unit 302 and the measuring light is to be emitted when the rotation of the optical probe is started.

In step S2606, it is judged whether or not the rotation of the optical probe 1601 is stopped based on the output of the encoder unit 1606. In step S2606, in a case in which it is judged that the optical probe 1601 does not rotate, the flow proceeds to step S2607 and the shielding body 1801 is rotated to the close position by outputting a close command with respect to the shutter control unit 1635.

In step S2608, it is judged whether or not the catheter unit 301 is in a disconnection state. In a case in which it is judged in step S2608 that the catheter unit 301 is in a disconnection state, the flow returns to step S2602 and it is observed whether or not the catheter unit 301 is connected.

On the other hand, in a case in which it is judged in step S2608 that the catheter unit 301 is not in a disconnection state, the drive/non-drive of the wavelength-swept light source 1608 is confirmed in step S2609 and thereafter, the flow returns to step S2602.

In this manner, in the signal processing unit 1623, a shutter opening and closing process is executed during a period when the wavelength-swept light source 1608 is driven and the measuring light is emitted only during a period when the catheter unit 301 is disconnected and during a period the catheter unit 301 is connected and also the optical probe rotates. In addition, the shutter is closed to not emit the measuring light in a case in which the optical probe does not rotate, although the catheter unit 301 is connected.

According to the optical coherent tomography diagnosis apparatus relating to the present exemplified embodiment, the measuring light will never be emitted if it is not in a state in which the catheter unit is disconnected or in a state in which the catheter unit is connected and also the optical probe rotates, even in a case in which the wavelength-swept light source is driven. It is thus possible to avoid reception of the measuring light before and after the diagnosis.

The present exemplified embodiment was explained with respect to a situation in which the shutter unit 1637 is controlled, but it is possible to execute a similar process also in case of controlling the frequency shifter unit 2001.

Fourteenth Exemplified Embodiment

The eighth to the thirteenth exemplified embodiments described above employ a construction in which a material not passing through the measuring light is used as a shielding body, but the present invention is not limited in this way. For example, it may be a material which can be reduced for the amount of the passing-through light until a level which has no-problem even if being light-received for a long time period continuously.

Also, the tenth to the thirteenth exemplified embodiments mentioned above employ a construction in which the shutter opening and closing process or the control process of the frequency shifter is executed based on the output from the encoder unit detecting the rotation of the optical probe. However, the apparatus intended to be encompassed here is not limited in this way, and it is also possible to employ a construction in which the control of the shutter opening and closing process or the process of the frequency shifter is executed based on the rotation command of the optical probe. Alternatively, it is also possible to employ a construction in which a sensor for detecting the rotation of the optical probe is provided separately from the encoder unit and the shutter opening and closing process or the control process of the frequency shifter is executed based on the output of the sensor thereof.

The principles, embodiments and modes of operation of the apparatus have been described in the foregoing specification, but the invention which is intended to be protected is not to be construed as limited to the particular embodiments of the apparatus disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An image diagnostic apparatus comprising:
 a light source;
 a probe connected to the light source to transmit light from the light source and receive reflection light in a body cavity by rotatingly scanning the probe in the body cavity to permit formation of a tomographic image in the body cavity based on the reflection light;
 a first branch portion for branching the light transmitted to the probe;
 a sample light path branched on the sample side by the first branch portion;
 a reference light path branched on the reference side by the first branch portion;
 a light transmission permitting and preventing device positioned along the sample light path, the light transmission permitting and preventing device possessing an incident port and an emission port;
 a control unit connected to the light transmission permitting and preventing device for controlling the light transmission permitting and preventing device to either permit the light at the incident port to exit out of the emission port or to prevent light at the incident port from exiting out of the emission port;
 the light transmission permitting and preventing device comprising one of: a shutter unit in which a movable shutter is positioned in a housing and is controlled by the control unit to move between one position permitting the light at the incident port to exit out of the emission port and another position preventing light at the incident port from exiting out of the emission port; and a frequency shifter unit controlled by the control unit to shift a frequency of light at the input port to either permit or prevent the light at the inlet port to exit the frequency shifter at the emission port; and
 a connection detector which detects connection of the probe, the control unit controlling the light transmission permitting and preventing device based on information from the connection detector.

2. The image diagnostic apparatus according to claim 1, further comprising a second branch portion for branching reflection light from the sample to a light detector unit on the sample light path, wherein the frequency shifter exists between the first branch portion and the second branch portion.

3. An image diagnostic apparatus comprising:
 a probe adapted to be connected to a light source to transmit light from the light source and receive reflection light in a body cavity by rotatingly scanning the probe in the body cavity to permit formation of a tomographic image in the body cavity based on the reflection light;
 a light-shield positioned upstream of the probe with respect to a direction of light transmission to selectively shield the probe from the light from the light source;
 a connection detector for detecting whether or not the probe is connected; and
 a controller connected to the light shield to control the light-shield based on a result detected by the connection detector to either shield the probe from the light from the light source or permit the light to transmit to the probe.

4. The image diagnostic apparatus according to claim 3, wherein the light-shield is a shielding body that shields the probe by moving the shielding body from a non-shielding position to a shielding position.

5. The image diagnostic apparatus according to claim 3, wherein the light-shield shields the light transmitted to the probe by changing a light path of the light transmitted to the probe so as to be illuminated on a shielding body arranged upstream.

6. The image diagnostic apparatus according to claim 3, wherein the light-shield is a frequency shifter comprises a housing, having a light incident port and a light emission port, and an acoustooptical device positioned in the housing to selectively diffract incident light from the light incident port of the housing and permit light-emission from the light emission port of the housing;
 the acoustooptical device being operable by an RE signal such that when an RF signal is input to the acoustooptical device, light-emission from the light emission port is permitted by diffracting the incident light; and
 when an RF signal is not input to the acoustooptical device, the incident light is illuminated toward the housing to prevent the light emission from the light emission port.

7. The image diagnostic apparatus according to claim 3, wherein the controller controls the light-shield such that the light is transmitted to the probe when the connection detector detects that the probe is connected.

8. The image diagnostic apparatus according to claim 3, wherein the controller controls the light-shield such that the light is transmitted to the probe for a predetermined time period when the connection detector detects that the probe is connected.

9. The image diagnostic apparatus according to claim 3, further comprising a rotation detector for detecting rotation of the probe, the controller controlling the light-shield such that the light is transmitted to the probe when the connection detector detects that the probe is connected and the rotation detector detects that the probe is rotating.

10. The image diagnostic apparatus according to claim 3, further comprising a rotation detector for detecting rotation of the probe, the controller controlling the light-shield such that the light is shielded from being transmitted to the probe when the connection detector detects that the probe is connected and such that the light is transmitted to the probe when the rotation detector detects that the probe is rotating.

11. The image diagnostic apparatus according to claim 3, further comprising a fiber connected to the light source, the light source being a low coherence source.

12. The image diagnostic apparatus according to claim 3, further comprising a fiber connected to the light source, the light source being a light source outputting a wavelength swept laser light.

13. A method of operating an image diagnostic apparatus in which a probe positioned in a body cavity transmits light from a light source and receives reflection light in the body cavity by rotatingly scanning the probe in the body cavity to permit formation of a tomographic image in the body cavity based on the reflection light, the method comprising;
   detecting whether the probe is connected to the light source; and
   using a result of the detection of whether the probe is connected to the light source to determine whether to permit the light to be transmitted to the probe or to prevent the light from being transmitted to the probe.

14. The method according to claim 13, further comprising detecting whether the probe is rotating, and permitting the light to be transmitted to the probe when it is detected that the probe is connected to the light source and when it is detected that the probe is rotating.

15. The method according to claim 13, further comprising permitting the light to be transmitted to the probe when it is detected that the probe is connected.

16. The method according to claim 13, further comprising detecting whether the probe is rotating, and preventing the light from being transmitted to the probe when it is detected that the probe is not rotating.

17. The method according to claim 13, further comprising determining whether light-emitting instructions exist, and preventing transmission of the light to the probe after permitting the light to be transmitted to the probe for a predetermined time following determination that the light-emitting instructions exist.

18. A computer readable recording medium stored with a control program for performing the method according to claim 13 by way of a computer.

* * * * *